United States Patent
Bren et al.

(10) Patent No.: US 8,815,533 B2
(45) Date of Patent: Aug. 26, 2014

(54) METHOD AND SYSTEM FOR PURIFYING AND QUANTITATING PROTEINS USING HEME FUSION TAGS

(75) Inventors: Kara L. Bren, Rochester, NY (US); Wesley B. Asher, New York, NY (US)

(73) Assignee: University of Rochester, Rochester, NY (US)

( * ) Notice: Subject to any disclaimer, the term of this patent is extended or adjusted under 35 U.S.C. 154(b) by 0 days.

(21) Appl. No.: 13/576,038

(22) PCT Filed: Jan. 28, 2011

(86) PCT No.: PCT/US2011/022982
§ 371 (c)(1),
(2), (4) Date: Oct. 4, 2012

(87) PCT Pub. No.: WO2011/094584
PCT Pub. Date: Aug. 4, 2011

(65) Prior Publication Data
US 2013/0203101 A1      Aug. 8, 2013

Related U.S. Application Data

(60) Provisional application No. 61/299,965, filed on Jan. 30, 2010.

(51) Int. Cl.
| | | |
|---|---|---|
| *C12Q 1/04* | (2006.01) | |
| *C12Q 1/02* | (2006.01) | |
| *C12Q 1/06* | (2006.01) | |
| *C12P 13/24* | (2006.01) | |
| *C12P 13/04* | (2006.01) | |
| *C12P 13/08* | (2006.01) | |

(52) U.S. Cl.
USPC ............................. 435/29; 435/39; 435/107

(58) Field of Classification Search
None
See application file for complete search history.

(56) References Cited

U.S. PATENT DOCUMENTS

2006/0281906 A1    12/2006   Johnson et al.

OTHER PUBLICATIONS

Braun et al. "A heme tag for in vivo synthesis of artifical cytochromes" 2005 Appl. Microbiol. Biotechnol. 67: 234-239.*
Suga et al. "Heme content of Catalse I from *Bacillus stearothermophilus*" 1996 Journal of Fermentation and Bioengineering 81: 259-261.*
Lill et al. "Import of cytochrome c heme lyase into mitochondira: a novel pathway into the intermembrane space" 1992 EMBO J. 11: 449-456.*
Beckett et al. "Four genes are required for the system II cytochrome c biogenesis pathway in *Bordetella pertussis*, a unique bacterial model" 2000 Molecular Microbiology 38: 465-481.*
Palmer et al. "Moving folded proteins across the bacterial cell membrane" 2003 Microbiology 149: 547-556.*
Berry et al. "Simultaneous determination of Hemes a, b, c from pyridine hemochrome spectra" 1987 Analytical Biochemistry 161: 1-15.*
International Search Report and Written Opinion of the International Searching Authority (KIPO) for International Application No. PCT/US2011/022982 dated Oct. 31, 2011 (8 pages).
Finn, Robert D. et al., Rainbow tags: a visual tag system for recombinant protein expression and purification, 2005 BioTechniques, vol. 38, No. 3 (pp. 387-392).
Braun, Martin et al., "A heme tag for in vivo synthesis of artificial cytochromes", 2005 Appl. Microbiol. Biotechnol., vol. 67 (pp. 234-239).
Braun, Martin et al., Biosynthesis of artificial microperoxidases by exploiting the secretion and cytochrome c maturation apparatuses of *Escherichia coli*, Aug. 31, 2004, PNAS, vol. 101, No. 35 (pp. 12830-12835).
Asher, Wesley B. et al., "A heme fusion tag for protein affinity purification and quantification", 2010 Protein Science, vol. 19 (pp. 1830-1839).

* cited by examiner

*Primary Examiner* — Suzanne M Noakes
*Assistant Examiner* — Gerard Lacourciere
(74) *Attorney, Agent, or Firm* — Harris Beach PLLC

(57) ABSTRACT

A method is provided for purifying a protein comprising the steps of providing a heme tag with an open coordination site and tagging the recombinant protein of interest with the heme tag. A resin framework is used, wherein a base that binds to heme is immobilized to the resin, and the open coordination site of the heme tag is capable of reversibly binding to the base immobilized to the resin. The tagged protein is reversibly bound to the resin, then eluted from the resin and quantified. The method enables the tagged protein to be tracked during protein expression or purification, and can be used to identify secretion of a protein to the periplasm or to tag proteins in the cytoplasm.

25 Claims, 10 Drawing Sheets

Figure 1:
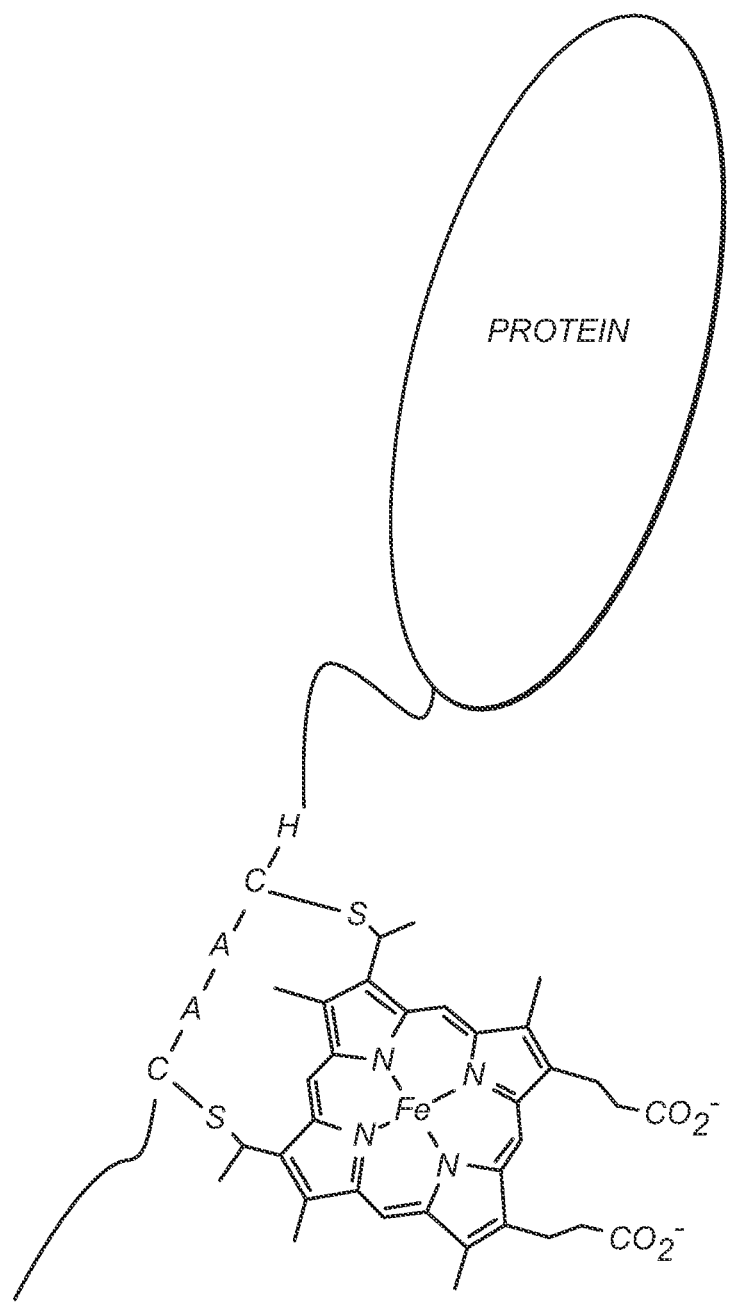

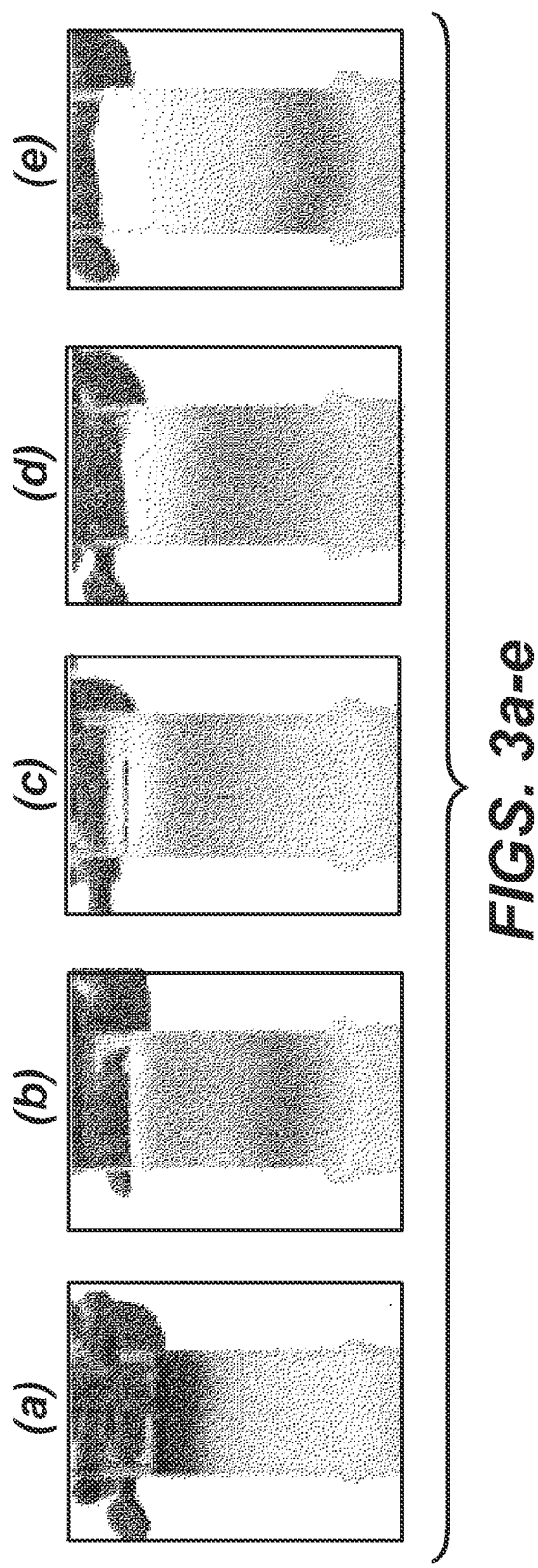
FIGS. 3a-e

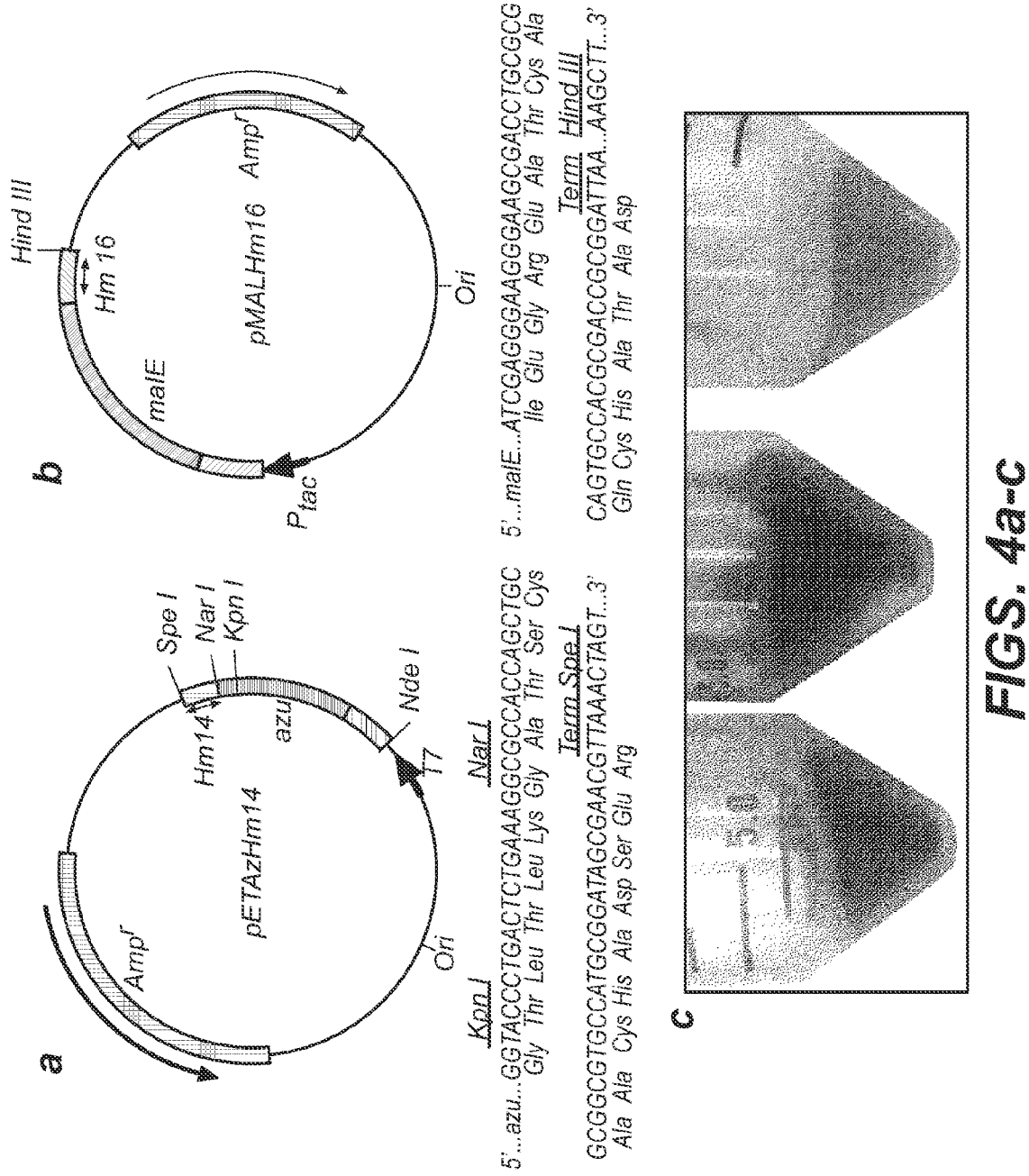
FIGS. 4a-c

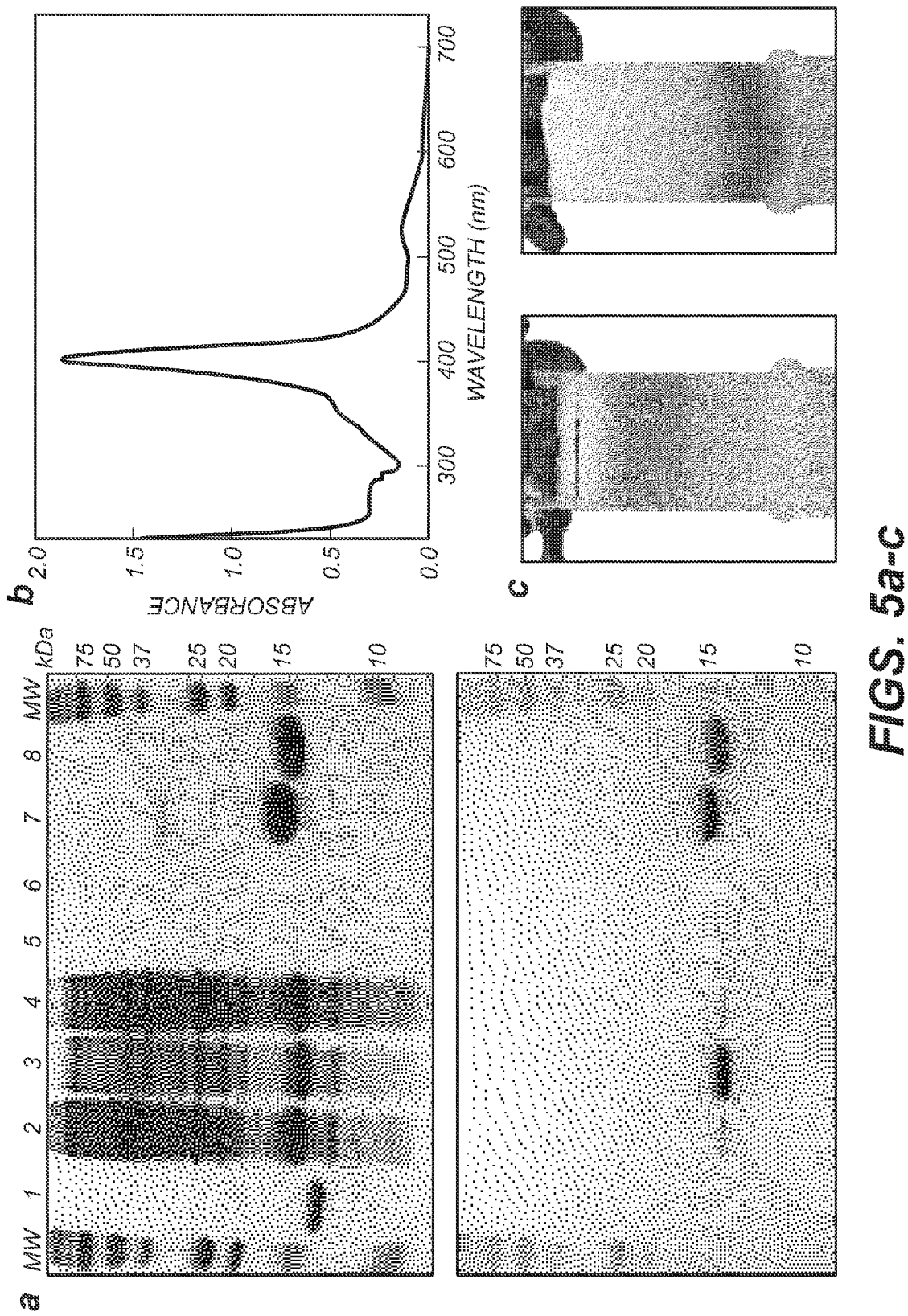
FIGS. 5a-c

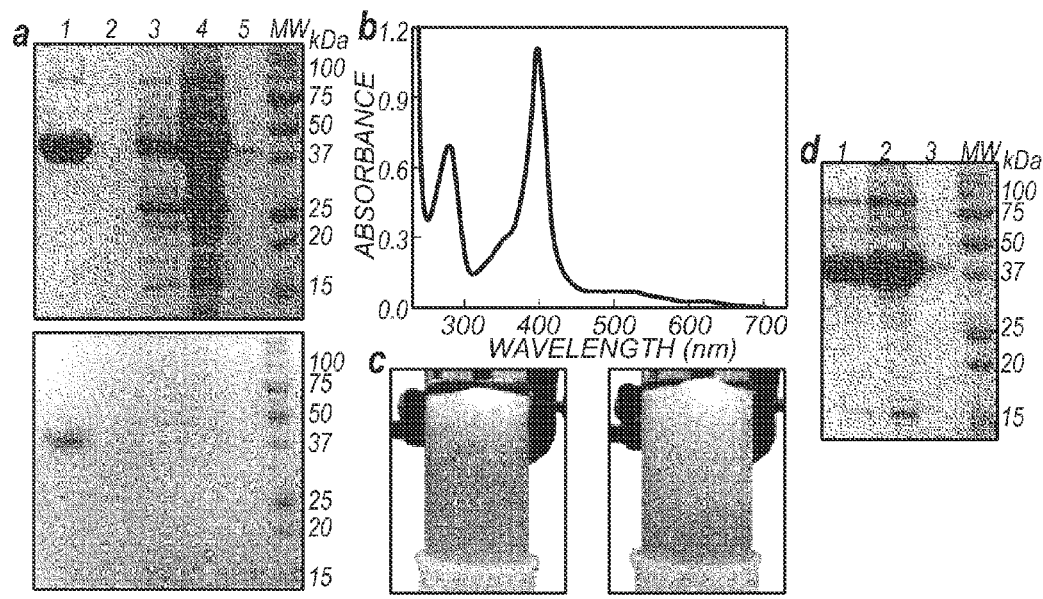
FIGS. 6a-d
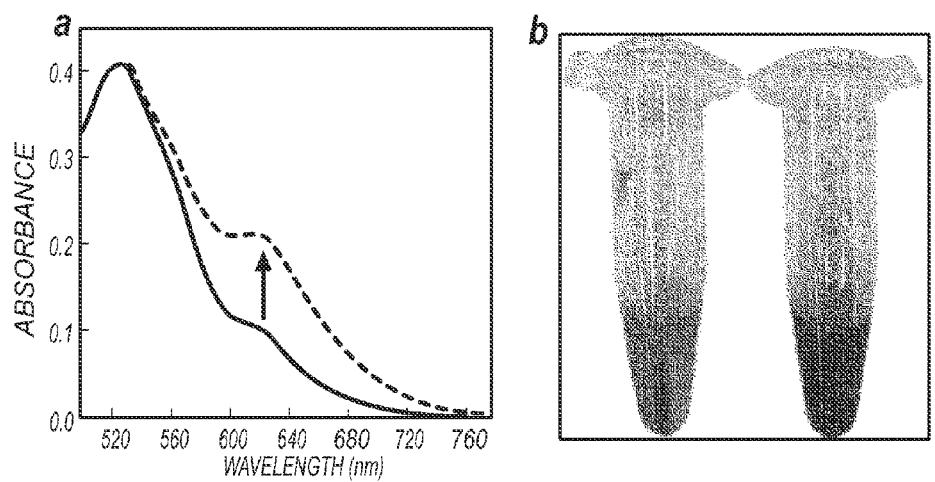
FIGS. 7a-b

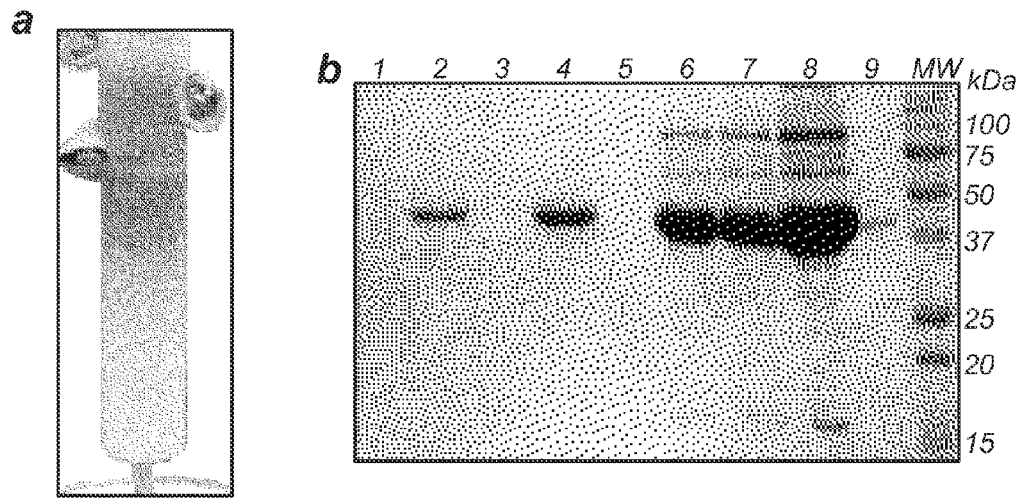
FIGS. 8a-b
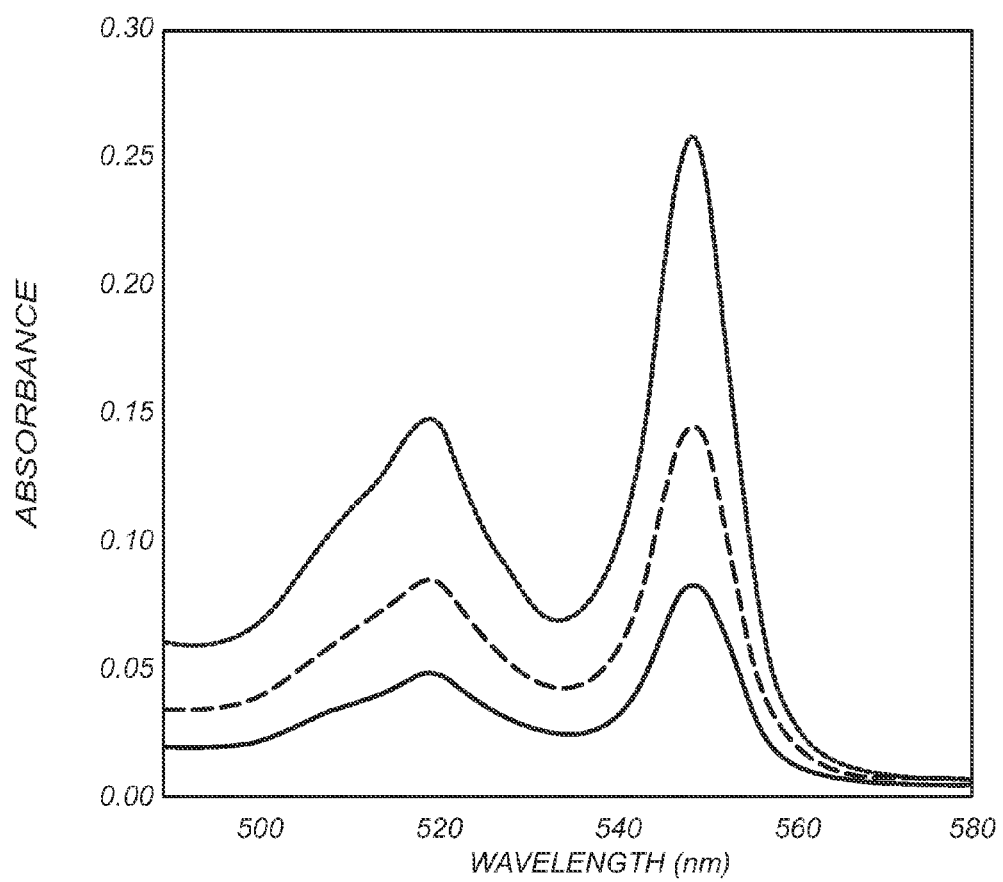
FIG. 9

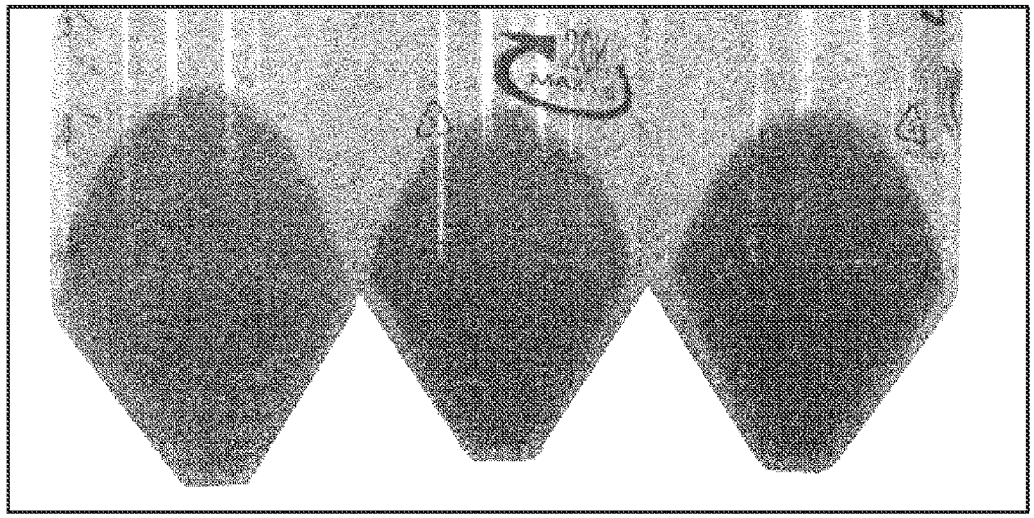
FIG. 14
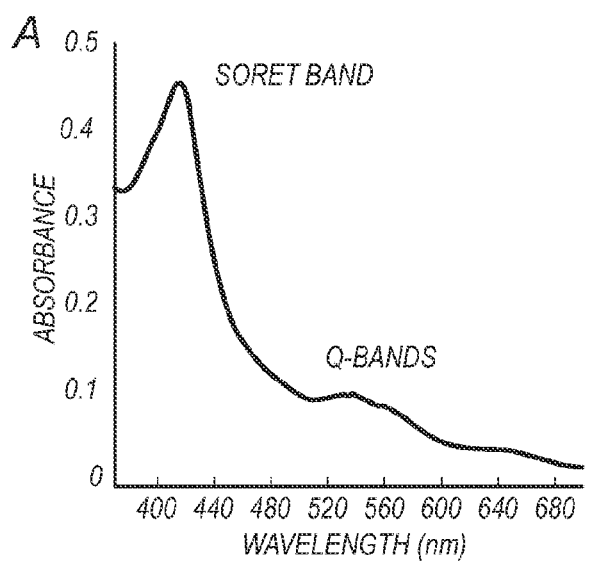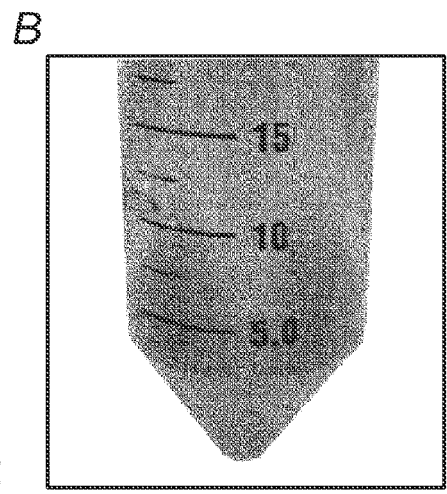
FIG. 15A-B

```
                            SEQUENCE LISTING

<160> NUMBER OF SEQ ID NOS: 38

<210> SEQ ID NO 1
<211> LENGTH: 5
<212> TYPE: PRT
<213> ORGANISM: Artificial Sequence
<220> FEATURE:
<223> OTHER INFORMATION: Synthesized Sequence

<400> SEQUENCE: 1

Cys Ala Ala Cys His
1               5

<210> SEQ ID NO 2
<211> LENGTH: 5
<212> TYPE: PRT
<213> ORGANISM: Artificial Sequence
<220> FEATURE:
<223> OTHER INFORMATION: Synthesized Sequence

<400> SEQUENCE: 2

Cys Ala Gln Cys His
1               5

<210> SEQ ID NO 3
<211> LENGTH: 5
<212> TYPE: PRT
<213> ORGANISM: Artificial Sequence
<220> FEATURE:
<223> OTHER INFORMATION: Synthesized Sequence

<400> SEQUENCE: 3

Cys Ala Glu Cys His
1               5

<210> SEQ ID NO 4
<211> LENGTH: 5
<212> TYPE: PRT
<213> ORGANISM: Artificial Sequence
<220> FEATURE:
<223> OTHER INFORMATION: Synthesized Sequence

<400> SEQUENCE: 4

Cys Trp Ala Cys His
1               5

<210> SEQ ID NO 5
<211> LENGTH: 14
<212> TYPE: PRT
<213> ORGANISM: Artificial Sequence
<220> FEATURE:
<223> OTHER INFORMATION: Synthesized Sequence

<400> SEQUENCE: 5

Ser Thr Ala Gly Cys Ala Ala Cys His Ala Asp Ser Glu Arg
1               5                   10

<210> SEQ ID NO 6
<211> LENGTH: 21
<212> TYPE: PRT
<213> ORGANISM: Artificial Sequence
<220> FEATURE:
<223> OTHER INFORMATION: Synthesized Sequence

<400> SEQUENCE: 6
```

```
Ser Thr Ala Gly Cys Ala Ala Cys His Ala Asp Ser Glu Arg His His
1               5                   10                  15

His His His His His
            20
```

```
<210> SEQ ID NO 7
<211> LENGTH: 29
<212> TYPE: PRT
<213> ORGANISM: Artificial Sequence
<220> FEATURE:
<223> OTHER INFORMATION: Synthesized Sequence

<400> SEQUENCE: 7

Gly Asp Val Glu Lys Gly Lys Lys Ile Phe Val Gln Lys Cys Ala Gln
1               5                   10                  15

Cys His Thr Val Glu Lys Gly Gly Lys His Lys Thr Gly
            20                  25
```

```
<210> SEQ ID NO 8
<211> LENGTH: 6
<212> TYPE: PRT
<213> ORGANISM: Artificial Sequence
<220> FEATURE:
<223> OTHER INFORMATION: Synthesized Sequence

<400> SEQUENCE: 8

His His His His His His
1               5
```

```
<210> SEQ ID NO 9
<211> LENGTH: 14
<212> TYPE: PRT
<213> ORGANISM: Artificial Sequence
<220> FEATURE:
<223> OTHER INFORMATION: Synthesized Sequence

<400> SEQUENCE: 9

Gly Ala Thr Ser Cys Ala Ala Cys His Ala Asp Ser Glu Arg
1               5                   10
```

```
<210> SEQ ID NO 10
<211> LENGTH: 20
<212> TYPE: PRT
<213> ORGANISM: Artificial Sequence
<220> FEATURE:
<223> OTHER INFORMATION: Synthesized Sequence

<400> SEQUENCE: 10

Gly Ala Thr Ser Cys Ala Ala Cys His Ala Asp Ser Glu His His
1               5                   10                  15

His His His His
            20
```

```
<210> SEQ ID NO 11
<211> LENGTH: 16
<212> TYPE: PRT
<213> ORGANISM: Artificial Sequence
<220> FEATURE:
<223> OTHER INFORMATION: Synthesized Sequence

<400> SEQUENCE: 11

Ile Glu Gly Arg Glu Ala Thr Cys Ala Gln Cys His Ala Thr Ala Asp
1               5                   10                  15
```

<210> SEQ ID NO 12
<211> LENGTH: 15
<212> TYPE: PRT
<213> ORGANISM: Artificial Sequence
<220> FEATURE:
<223> OTHER INFORMATION: Synthesized Sequence

<400> SEQUENCE: 12

Asn Ser Arg Tyr Pro Ala Ala Cys Leu Ala Cys His Ala Ile Gly
1               5                   10                  15

<210> SEQ ID NO 13
<211> LENGTH: 75
<212> TYPE: DNA
<213> ORGANISM: Artificial Sequence
<220> FEATURE:
<223> OTHER INFORMATION: Synthesized Sequence

<400> SEQUENCE: 13
atgaaaggta ccctgactct gaaaggcgcc accagctgcg cggcgtgcca tgcggatagc    60
gaacattaaa ctagt                                                    75

<210> SEQ ID NO 14
<211> LENGTH: 30
<212> TYPE: DNA
<213> ORGANISM: Artificial Sequence
<220> FEATURE:
<223> OTHER INFORMATION: Synthesized Sequence

<400> SEQUENCE: 14
atgaaaggta ccctgactct gaaaggcgcc                                    30

<210> SEQ ID NO 15
<211> LENGTH: 29
<212> TYPE: DNA
<213> ORGANISM: Artificial Sequence
<220> FEATURE:
<223> OTHER INFORMATION: Synthesized Sequence

<400> SEQUENCE: 15
atcagtttaa tgttcgctat gcgcatgcg                                     29

<210> SEQ ID NO 16
<211> LENGTH: 38
<212> TYPE: DNA
<213> ORGANISM: Artificial Sequence
<220> FEATURE:
<223> OTHER INFORMATION: Synthesized Sequence

<400> SEQUENCE: 16
gccatgcgga tagcgaacgt taaactagta acggccgc                           38

<210> SEQ ID NO 17
<211> LENGTH: 38
<212> TYPE: DNA
<213> ORGANISM: Artificial Sequence
<220> FEATURE:
<223> OTHER INFORMATION: Synthesized Sequence

<400> SEQUENCE: 17
cgcgccgtta ctagtttaac gttcgctatc cgcatggc                           38

<210> SEQ ID NO 18
<211> LENGTH: 78
<212> TYPE: DNA
<213> ORGANISM: Artificial Sequence
<220> FEATURE:
<223> OTHER INFORMATION: Synthesized Sequence

<400> SEQUENCE: 18
atgaaaggta ccctgactgt gaaaaacagc cgttatccgg cggcgtgcct ggcgtgccat    60
gcgattggct aaactagt                                                 78

<210> SEQ ID NO 19
<211> LENGTH: 32
<212> TYPE: DNA
<213> ORGANISM: Artificial Sequence
<220> FEATURE:
<223> OTHER INFORMATION: Synthesized Sequence

<400> SEQUENCE: 19
atgaaaggta ccctgactct gaaaaacagc cg                                 32

<210> SEQ ID NO 20
<211> LENGTH: 31
<212> TYPE: DNA
<213> ORGANISM: Artificial Sequence
<220> FEATURE:
<223> OTHER INFORMATION: Synthesized Sequence

<400> SEQUENCE: 20
actagtttag ccaatcgcat ggcacgccag g                                  31

<210> SEQ ID NO 21
<211> LENGTH: 108
<212> TYPE: DNA
<213> ORGANISM: Artificial Sequence
<220> FEATURE:
<223> OTHER INFORMATION: Synthesized Sequence

<400> SEQUENCE: 21
gaagcgacct gcgcgcagtg ccacgcgacc gcggatgcgt gcgcgcagtg ccacgcgacc    60
gcggatgcgt gcgcgcagtg ccacaccgcg aataaaagc ttatatat                108

<210> SEQ ID NO 22
<211> LENGTH: 30
<212> TYPE: DNA
<213> ORGANISM: Artificial Sequence
<220> FEATURE:
<223> OTHER INFORMATION: Synthesized Sequence

<400> SEQUENCE: 22
gaagcgacct gcgcgcagtg ccacgcgacc                                    30

<210> SEQ ID NO 23
<211> LENGTH: 38
<212> TYPE: DNA
<213> ORGANISM: Artificial Sequence
<220> FEATURE:
<223> OTHER INFORMATION: Synthesized Sequence

<400> SEQUENCE: 23
atatataagc ttttattccg cggtgtggca ctgcgcgc                           38

<210> SEQ ID NO 24
<211> LENGTH: 34
<212> TYPE: DNA
<213> ORGANISM: Artificial Sequence
<220> FEATURE:
<223> OTHER INFORMATION: Synthesized Sequence

```
<400> SEQUENCE: 24
cacgcgaccg cggattaatg cgcggagtgc cacg                          34

<210> SEQ ID NO 25
<211> LENGTH: 34
<212> TYPE: DNA
<213> ORGANISM: Artificial Sequence
<220> FEATURE:
<223> OTHER INFORMATION: Synthesized Sequence

<400> SEQUENCE: 25
cgtggcactg cgcgcattaa tccgcggtcg cgtg                          34

<210> SEQ ID NO 26
<211> LENGTH: 93
<212> TYPE: DNA
<213> ORGANISM: Artificial Sequence
<220> FEATURE:
<223> OTHER INFORMATION: Synthesized Sequence

<400> SEQUENCE: 26
atgaaaggta ccctgactct gaaaggcgcc accagctgcg cggcgtgcca tgcggatagc    60
gaacatcatc atcatcatca tcattaaact agt                                 93

<210> SEQ ID NO 27
<211> LENGTH: 30
<212> TYPE: DNA
<213> ORGANISM: Artificial Sequence
<220> FEATURE:
<223> OTHER INFORMATION: Synthesized Sequence

<400> SEQUENCE: 27
atgaaaggta ccctgactct gaaaggcgcc                               30

<210> SEQ ID NO 28
<211> LENGTH: 42
<212> TYPE: DNA
<213> ORGANISM: Artificial Sequence
<220> FEATURE:
<223> OTHER INFORMATION: Synthesized Sequence

<400> SEQUENCE: 28
actagtttaa tgatgatgat gatgatgatg ttcgctatcc gc                 42

<210> SEQ ID NO 29
<211> LENGTH: 14
<212> TYPE: PRT
<213> ORGANISM: Artificial Sequence
<220> FEATURE:
<223> OTHER INFORMATION: Synthesized Sequence

<400> SEQUENCE: 29

Ile Asp Gly Arg Cys Ala Ala Cys His Ala Asp Ser Glu Arg
1               5                   10

<210> SEQ ID NO 30
<211> LENGTH: 15
<212> TYPE: PRT
<213> ORGANISM: Artificial Sequence
<220> FEATURE:
<223> OTHER INFORMATION: Synthesized Sequence

<400> SEQUENCE: 30

Gly Ala Thr Ser Glu Cys Ala Ala Cys His Ala Asp Ser Glu Arg
1               5                   10                  15
```

```
<210> SEQ ID NO 31
<211> LENGTH: 16
<212> TYPE: PRT
<213> ORGANISM: Artificial Sequence
<220> FEATURE:
<223> OTHER INFORMATION: Synthesized Sequence

<400> SEQUENCE: 31

Gly Ala Thr Ser Glu Arg Cys Ala Ala Cys His Ala Asp Ser Glu Arg
1               5                   10                  15

<210> SEQ ID NO 32
<211> LENGTH: 17
<212> TYPE: PRT
<213> ORGANISM: Artificial Sequence
<220> FEATURE:
<223> OTHER INFORMATION: Synthesized Sequence

<400> SEQUENCE: 32

Gly Ala Thr Ser Glu Arg Asp Cys Ala Ala Cys His Ala Asp Ser Glu
1               5                   10                  15

Arg

<210> SEQ ID NO 33
<211> LENGTH: 20
<212> TYPE: PRT
<213> ORGANISM: Artificial Sequence
<220> FEATURE:
<223> OTHER INFORMATION: Synthesized Sequence

<400> SEQUENCE: 33

Gly Ala Thr Ser Cys Ala Ala Cys His Ala Asp Ser Glu His His His
1               5                   10                  15

His His His His
            20

<210> SEQ ID NO 34
<211> LENGTH: 16
<212> TYPE: PRT
<213> ORGANISM: Artificial Sequence
<220> FEATURE:
<223> OTHER INFORMATION: Synthesized Sequence

<400> SEQUENCE: 34

Arg Glu Ser Asp Ala Cys Ala Ala Cys His Ser Arg Gly Ser Thr Gly
1               5                   10                  15

<210> SEQ ID NO 35
<211> LENGTH: 31
<212> TYPE: PRT
<213> ORGANISM: Artificial Sequence
<220> FEATURE:
<223> OTHER INFORMATION: Synthesized Sequence

<400> SEQUENCE: 35

Val Glu Ala Phe Glu Lys Lys Cys Ala Glu Cys His Ser Lys Val Ala
1               5                   10                  15

Ala Phe Glu Ser Lys Cys Ala Glu Cys His His His His His
            20                  25                  30

<210> SEQ ID NO 36
<211> LENGTH: 21
<212> TYPE: PRT
<213> ORGANISM: Artificial Sequence
```

-continued

```
<220> FEATURE:
<223> OTHER INFORMATION: Synthesized Sequence

<400> SEQUENCE: 36

Val Glu Ala Phe Glu Lys Lys Val Ala Ala Phe Glu Ser Lys Cys Ala
1               5                   10                  15

Ala Cys His Ala Lys
            20

<210> SEQ ID NO 37
<211> LENGTH: 13
<212> TYPE: PRT
<213> ORGANISM: Artificial Sequence
<220> FEATURE:
<223> OTHER INFORMATION: Synthesized Sequence

<400> SEQUENCE: 37

Gly Tyr Ala Ser Cys Trp Ala Cys His Glu Glu Glu Glu
1               5                   10

<210> SEQ ID NO 38
<211> LENGTH: 22
<212> TYPE: PRT
<213> ORGANISM: Artificial Sequence
<220> FEATURE:
<223> OTHER INFORMATION: Synthesized Sequence

<400> SEQUENCE: 38

His Ser Ser Tyr Trp Tyr Ala Phe Asn Asn Lys Thr Gly Cys Ala Ala
1               5                   10                  15

Cys His Glu Glu Glu Glu
            20
```

METHOD AND SYSTEM FOR PURIFYING AND QUANTITATING PROTEINS USING HEME FUSION TAGS

CROSS-REFERENCE TO RELATED APPLICATIONS

This application is a national stage application under 35 U.S.C. §371 of PCT Application No. PCT/US2011/022982, entitled "Method and System For Purifying and Quantitating Proteins Using Heme Fusion Tags," filed Jan. 28, 2011, which claims priority to and the benefit of U.S. provisional patent application Serial No. 61/299,965, entitled "Use of a heme fusion tag for protein purification and quantitation," filed Jan. 30, 2010, which is incorporated herein by reference in its entirety.

STATEMENT REGARDING FEDERALLY SPONSORED RESEARCH OR DEVELOPMENT

The disclosed invention was made with government support under grant no. PHY-0646565 from the National Science Foundation and grant no. GM63170 from the National Institutes of Health. The government has rights in this invention.

1. TECHNICAL FIELD

The present invention relates to methods for adding heme peptide fusion tags to recombinant proteins. The invention further relates to methods for affinity purifying proteins using heme peptide fusion tags. The invention also relates to methods for quantitating proteins using heme peptide fusion tags. The invention also relates to peptide fusion systems based on heme tags with open coordination sites.

2. BACKGROUND OF THE INVENTION

The addition of peptide and protein fusion tags to recombinant proteins is widely employed in biochemical studies (Terpe, K. Overview of tag protein fusions: from molecular and biochemical fundamentals to commercial systems. Appl. Microbiol. Biotechnol. 60, 523-533 (2003); Chelur, D., Unal, O., Scholtyssek, M. & Strickler, J. Fusion tags for protein expression and purification. in BioPharm Int. 2008 June supplement, Guide to Protein Production 38-46, Advanstar Communications, Inc., Woodland Hills, Calif., 2008). Fusion tags exist for a variety of applications, including affinity purification, solubility enhancement, and protein detection (Terpe, K. Overview of tag protein fusions: from molecular and biochemical fundamentals to commercial systems. Appl. Microbiol. Biotechnol. 60, 523-533 (2003); Chelur, D., Unal, O., Scholtyssek, M. & Strickler, J. Fusion tags for protein expression and purification. in BioPharm Int. 2008 June supplement, Guide to Protein Production 38-46 (Advanstar Communications, Inc., Woodland Hills, Calif., 2008); Nilsson, J., Stahl, S., Lundeberg, J., Uhlen, M. & Nygren, P.A. Affinity fusion strategies for detection, purification, and immobilization of recombinant proteins. Protein Expr. Purif. 11, 1-16 (1997); Arnau, J., Lauritzen, C., Petersen, G.E. & Pedersen, J. Current strategies for the use of affinity tags and tag removal for the purification of recombinant proteins. Protein Expr. Purif. 48, 1-13 (2006); Lichty, J.J., Malecki, J.L., Agnew, H.D., Michelson-Horowitz, D.J. & Tan, S. Comparison of affinity tags for protein purification. Protein Expr. Purif. 41, 98-105 (2005)). Affinity purification methods are popular because they can dramatically lower purification time, often require minimal purification steps, and can be used to obtain greater than 90% purity with high yields (Terpe, K. Overview of tag protein fusions: from molecular and biochemical fundamentals to commercial systems. Appl. Microbiol. Biotechnol. 60, 523-533 (2003); Nilsson, J., Stahl, S., Lundeberg, J., Uhlen, M. & Nygren, P.A. Affinity fusion strategies for detection, purification, and immobilization of recombinant proteins. Protein Expr. Purif. 11, 1-16 (1997); Lichty, J.J., Malecki, J.L., Agnew, H. D., Michelson-Horowitz, D.J. & Tan, S. Comparison of affinity tags for protein purification. Protein Expr. Purif. 41, 98-105 (2005)). However, affinity-tagged proteins are purified using conditions (buffer, additives, etc.) specific to the fusion tag, and not the protein of interest (Chelur, D., Unal, O., Scholtyssek, M. & Strickler, J. Fusion tags for protein expression and purification. in BioPharm Int. 2008 June supplement, Guide to Protein Production 38-46 (Advanstar Communications, Inc., Woodland Hills, Calif., 2008)). Thus, no single affinity procedure can be used to purify every protein, resulting in the need for a wide variety of fusion tags and the continuing development of novel affinity purification methods (Chelur, D., Unal, O., Scholtyssek, M. & Strickler, J. Fusion tags for protein expression and purification. in BioPharm Int. 2008 June supplement, Guide to Protein Production 38-46 (Advanstar Communications, Inc., Woodland Hills, Calif., 2008)). Recently, fusion tags detectable by the naked eye have been developed for continuous tracking of protein expression, production, and purification (Chelur, D., Unal, O., Scholtyssek, M. & Strickler, J. Fusion tags for protein expression and purification. in BioPharm Int. 2008 June supplement, Guide to Protein Production 38-46 (Advanstar Communications, Inc., Woodland Hills, Calif., 2008)). For instance, protein fusions based on the yellow human flavin mononucleotide (FMN)-binding domain and the red mosquito cytochrome $b_5$ have been developed. In addition, the CHERRY™ Express (Delphi Genetics) kit for fusing an 11-kDa heme protein that also allows for protein quantitation is commercially available (Finn, R.D., Kapelioukh, L. & Paine, M.J.I. Rainbow tags: a visual tag system for recombinant protein expression and purification. Biotechniques 38, 387-392 (2005)). These colored tags aid visualization and quantitation, but for affinity purification, additional tags are needed.

Citation or identification of any reference in Section 2, or in any other section of this application, shall not be considered an admission that such reference is available as prior art to the present invention.

3. SUMMARY OF THE INVENTION

A method for purifying a protein (or peptide) of interest is provided. In one embodiment, the method comprises the steps of providing a heme tag with an open coordination site; and tagging the protein of interest with the heme tag.

In another embodiment, the method comprises the steps of providing a resin framework, wherein a base that binds to heme is immobilized to the resin, and the open coordination site of the heme tag is capable of reversibly binding to the base immobilized to the resin; and reversibly binding the tagged protein of interest to the resin.

In another embodiment, the base is an amine, pyridine, cyanide, or isocyanide or a derivative thereof.

In another embodiment, the base is L-histidine and the resin is an L-histidine immobilized agarose (HIS) resin.

In another embodiment, the method comprises, after the step of reversibly binding the tagged protein of interest to the resin, the step of eluting the protein of interest from the resin.

In another embodiment, the method comprises, after the step of eluting the protein of interest from the resin, the step of quantitating the eluted protein.

In another embodiment, the method comprises the step of visually tracking the tagged protein of interest during protein expression or protein purification.

In another embodiment, the method comprises the step of estimating or determining $\epsilon^P_{280}$.

In another embodiment, the protein of interest is expressed in a bacterial or yeast expression system.

In another embodiment, the expression system is an *Escherichia coli* or *Saccharomyces cerevisiae* expression system.

A method for identifying secretion of a protein (or peptide) of interest to the periplasm is also provided. In one embodiment, the method comprises the steps of providing a heme tag sequence fused to a protein of interest, wherein the heme tag sequence encodes a peptide that comprises a CXXCH motif; and attaching heme to the heme tag sequence with a cytochrome c maturation apparatus from a bacterium, thereby tagging the protein of interest with a heme tag, wherein heme-tagging of the protein is indicative of secretion to the periplasm.

In another embodiment, the bacterium is *E. coli*.

In another embodiment, the protein of interest is expressed in a bacterial expression system.

In another embodiment, the bacterial expression system is an *E. coli* expression system.

In another embodiment, the method comprises the step of screening for (e.g., visualization of) a color change in the bacteria, wherein the color change is indicative of secretion to periplasm.

In another embodiment, the screening step comprises preparing a cell pellet after expression of the protein of interest and screening for a color change in the cell pellet.

In another embodiment, the heme-tagged protein is a folded protein.

In another embodiment, the heme-tagged proteins are exported to periplasm via the twin-arginine translocation (Tat) system.

A method for cytoplasmic tagging of a protein (or peptide) of interest is also provided. In one embodiment, the method comprises the steps of providing a heme tag sequence fused to a protein of interest, wherein the heme tag sequence encodes a peptide that comprises a CXXCH motif; providing a fusion construct encoding a fusion protein wherein the N-terminal amino acids of mitochondrial cytochrome c are fused to the N-terminus of the protein of interest; and co-expressing the fusion construct and heme lyase gene in an expression system, thereby producing a heme-tagged fusion protein in the cytoplasm.

In one embodiment, the sequence of N-terminal amino acids is 5-10, 10-20, 20-30 or 30-50 amino acids long.

In another embodiment, the mitochondrial cytochrome c is capable of being expressed in the expression system using heme lyase for maturation.

In another embodiment, the expression system is a bacterial or yeast expression system.

In another embodiment, the expression system is an *Escherichia coli* or *Saccharomyces cerevisiae* expression system.

In another embodiment, the method comprises the step of screening for (e.g., visualization of) a color change in the bacteria or yeast, wherein the color change is indicative of cytoplasmic tagging of the protein of interest.

In another embodiment, the screening step comprises preparing a cell pellet after expression of the protein of interest and screening for a color change in the cell pellet.

In another embodiment, the method further comprises the steps of providing a resin framework, wherein a base that binds to heme is immobilized to the resin, and the heme tag comprises an open coordination site, wherein the open coordination site is capable of reversibly binding to the base immobilized to the resin; and reversibly binding the tagged protein of interest to the resin.

In another embodiment, the base is an amine, pyridine, cyanide, or isocyanide or a derivative thereof.

In another embodiment, the base is L-histidine and the resin is an L-histidine immobilized agarose (HIS) resin.

In another embodiment, the method comprises, after the step of reversibly binding the tagged protein of interest to the resin, the step of eluting the protein of interest from the resin.

In another embodiment, the method comprises, after the step of eluting the protein of interest from the resin, the step of quantitating the eluted protein.

A method for quantitating (or quantifying) a protein (or peptide) of interest is also provided. In one embodiment, the method comprises the steps of providing a heme tag with an open coordination site; tagging the protein of interest with the heme tag; providing a resin framework, wherein a base that binds to heme is immobilized to the resin, and the open coordination site of the heme tag is capable of reversibly binding to the base immobilized to the resin; reversibly binding the tagged protein of interest to the resin; eluting the protein of interest from the resin; and performing heme quantitation on the eluted protein, wherein the step of heme quantitation does not remove the heme tag.

In one embodiment, the step of heme quantitation comprises estimating or determining $\epsilon^P_{280}$.

In another embodiment, the base is an amine, pyridine, cyanide, or isocyanide or a derivative thereof.

In another embodiment, the base is L-histidine and the resin is an L-histidine immobilized agarose (HIS) resin.

A method for determining the extinction coefficient of a protein of interest at 280 nm ($\epsilon_{280}$) is also provided. In one embodiment, the method comprises heme-tagging a protein of interest; performing a pyridine hemochrome assay on the heme-tagged protein; subtracting the absorbance of the heme-tagged protein at 280 nm from absorbance of the heme tag at 280 nm to determine a remaining absorbance at 280 nm; using the remaining absorbance at 280 nm to determine the protein's $\epsilon_{280}$ through the relationship to a concentration determined from an extinction coefficient determined at 550 nm by the pyridine hemochrome assay.

A peptide fusion system comprising a heme tag is also provided. The heme tag can comprising a heme tag sequence fused to a protein of interest, wherein the heme tag sequence encodes a peptide that comprises a CXXCH motif, and a heme attached to the heme tag sequence.

In one embodiment, the CXXCH motif has any of the 20 standard amino acids as residues in the X position.

4. BRIEF DESCRIPTION OF THE DRAWINGS

The present invention is described herein with reference to the accompanying drawings, in which similar reference characters denote similar elements throughout the several views. It is to be understood that in some instances, various aspects of the invention may be shown exaggerated or enlarged to facilitate an understanding of the invention.

FIG. 1. Schematic of a heme tagged protein. The side chain of the His residue in the "CAACH" (SEQ ID NO:1) sequence binds to the heme iron (shown in FIGS. 2a-c), leaving one open site at the heme iron.

Figures 2A, 2B, 2C:
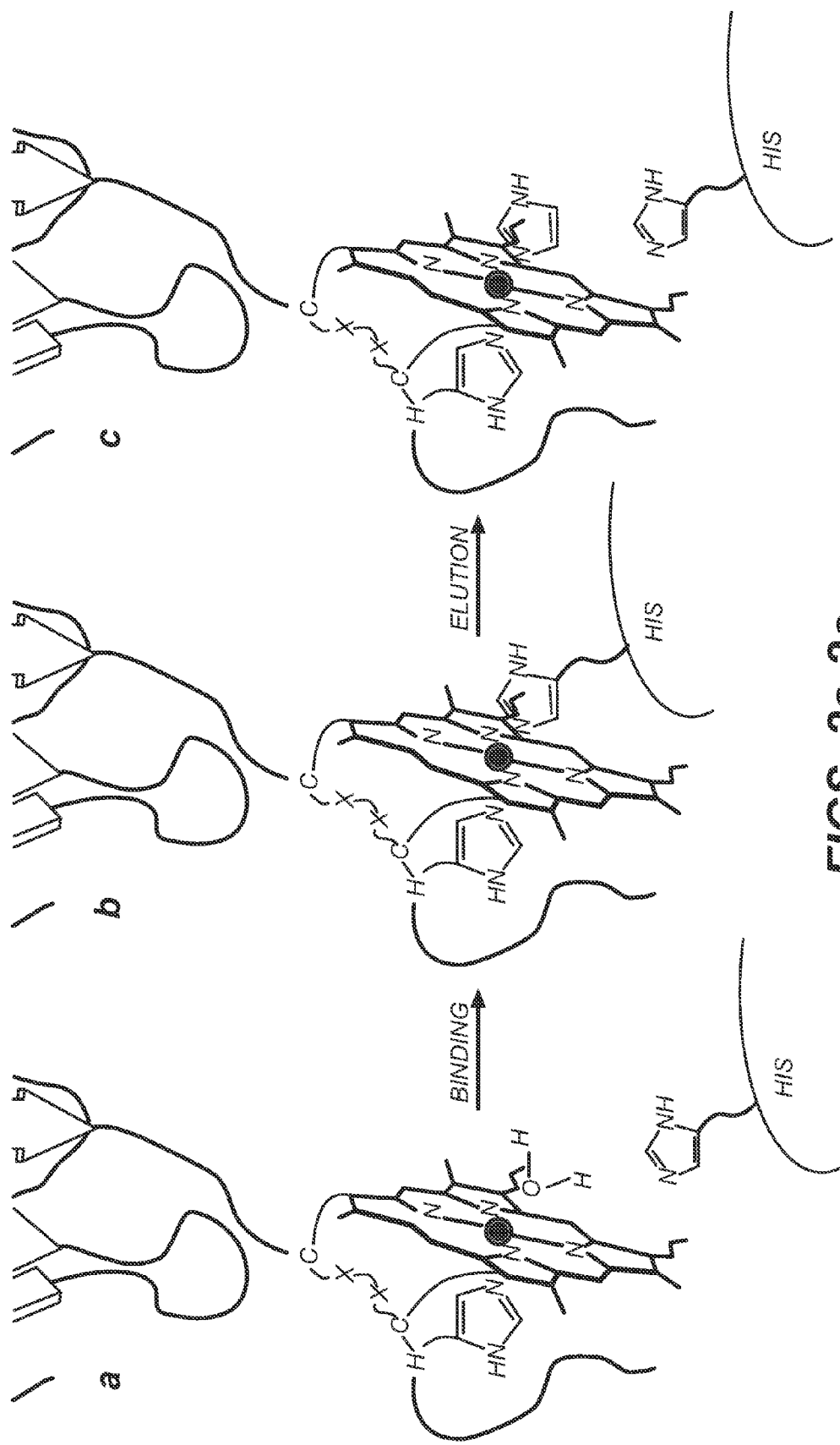

FIGS. 2a-c. Schematic of heme-tagged protein purification using the HIS resin. (a) Five-coordinate heme-tagged protein loaded onto to the HIS resin coordinating water or weakly coordinating another exogenous ligand. (b) Heme-tag binding to HIS column through coordination of immobilized histidine of the medium (HIS) and the iron of the heme tag. (c) Competitive elution of the protein by addition of free imidazole. Elution by low ($\leq 5$) or alkaline ($\geq 8$) pH buffer was also successfully used to elute the protein from the HIS resin.

FIGS. 3a-e. Purification of heme-tagged azurin on the HIS column (a) The heme-tagged azurin is loaded onto the column. The brown color indicates that the ligand to the heme is water. (b) As the heme-tagged azurin binds the HIS column, the heme turns pink Adding 0.5 column volumes (CV) of binding buffer (sodium phosphate) causes a green band (impurities) to elute from the column (c) After 1.5 CV of binding buffer, the pink band remains bound. (d-e) Eluting with 300 mM imidazole causes the desired product to elute from the column. The band stays pink because imidazole binds to the heme.

FIGS. 4a-c. Expression of Az-Hm14 and MBP-Hm16. (a) pETAzHm14 expression vector carrying the azurin expression gene made up of the Az structural gene (azu, dark gray portion between Nde I and Nar I restriction sites) and native signal sequence (light gray portion between Nde I and Kpn I restriction sites). The Hm14 sequence is shown between the NarI and SpeI restriction sites (double arrowhead). (b) pMALHm16 plasmid carrying the MBP expression gene sequence made up of the MBP structral gene (malE, dark gray portion between the Hm16 sequence and "$P_{tac}$" label) and native signal sequence (light gray portion between the Hm16 sequence and "$P_{tac}$" label). The Hm16 sequence is shown by the double arrowhead. (c) E. coli bacterial pellets containing Az-Hm20 (left), Az-Hm14 (middle), and a negative control pellet indicating background heme containing pET17b vector lacking a gene insert and containing pEC86 (right). The bacterial pellets containing overexpressed MBP-Hm16 and Az-MP301 are not shown, but were visually indistinguishable from that containing Az-Hm14.

FIGS. 5a-c. Purification of Az-Hm14 using the HIS resin. (a) 15% SDS-PAGE analysis of Az-Hm14 and Az-Hm20 after purification, developed in Coomassie (top) and heme stain (bottom). The samples loaded into both gels were derived from the same purification experiment, and the gels were processed and stained in parallel. Lane MW: molecular weight marker, 1: purified Az (see Section 6.1.7), 2: crude cellular extract from Az-Hm14 expression, 3: Partially clarified cellular extract from Az-Hm14 expression, 4: Fraction taken from HIS column after loading extract followed by 0.9 CV of binding buffer, 5: fraction taken after 2.0 CV, 6: blank, 7: Az-Hm20 purified using Ni(II) IMAC procedure, 8: Az-Hm14 purified using HIS column. (b) Absorption spectrum of Az-Hm14 in 25 mM NaP$_i$ pH 7.0 purified using the HIS resin. (c) Az-Hm14 binding to the HIS column after the addition of 2 CV of binding buffer (left) and after 1.5 CV of binding buffer containing 300 mM imidazole (right).

FIGS. 6a-d. Purification of MBP-Hm16 using the HIS resin. (a) 10% SDS-PAGE analysis of MBP-Hm16 purification, developed in Coomassie (top) and heme stain (bottom). The samples loaded into both gels were derived from the same purification experiment, and the gels were processed and stained in parallel. Lane MW: molecular weight marker, 1: MBP-Hm16 purified using the HIS column, 2: blank, 3: fraction taken from HIS column after loading extract followed by 0.9 CV of binding buffer, 4: crude periplasmic extract including MBP-Hm16, 5: Purified MBP (New England BioLabs, Ipswich, Mass.) (b) Absorption spectrum of MBP-Hm16 in 25 mM NaP$_i$ pH 7.0 purified using the HIS resin (c) MBP-Hm16 binding to the HIS column after the addition of 1.5 CV of binding buffer (left) and after 1.5 CV of binding buffer containing 300 mM imidazole (right). (d) 10% SDS-PAGE analysis of MBP-Hm16 purified using the amylose method. 1: fraction taken from HIS column after loading amylose-purified MBP-Hm16 (lane 2) followed by 0.9 CV of binding buffer, 2: MBP-Hm16 purified using the amylose method. The full-length gel is shown in shown in FIG. 8.

FIGS. 7a-b. To verify that Az-Hm14 retains its ability to coordinate copper ions, CuSO$_4$ was added to pure Az-Hm14 and the Cys(S)-to-Cu(II) charge-transfer band at 625 nm was monitored. (a) UV-vis spectra of Az-Hm14, 50 mM NaPi, pH 7.0 (solid line) and Az-Hm14 after the addition of 5-fold excess CuSO$_4$ (dotted line). The pH of the sample remained constant after the addition of CuSO$_4$ (b) Photograph of AzHm before the addition of CuSO$_4$ (left) and after (right). Both the intensity increase of the 625 nm absorption band and visible color change indicate that Az-Hm14 binds copper, and that the heme tag does not perturb copper binding.

FIGS. 8a-b. Protein purification using amylose resin. (a) Photograph of loading crude periplasm containing MBP-Hm16 on amylose resin. A distinct brown/green band formed on the top of the resin, and was washed with 12 CV of the recommended binding buffer to purify. The band eluted after the addition of 10 mM maltose dissolved in binding buffer. (b) Full-length 10% SDS PAGE gel developed with Coomassie stain shown in FIG. 6d. Lane 1: blank, 2 and 4: MBP-Hm16 purified using the HIS column after being partially clarified using an amylose resin, 3: blank, 5: blank, 6: Fraction taken from HIS column after addition of 1.3 column volume (CV) of binding buffer, 7: Fraction taken from HIS column after addition of 0.9 CV of binding buffer 8: Periplasmic extract purified using amylose resin, 9: Purified MBP (New England Biolabs), MW: Molecular weight marker.

FIG. 9. Pyridine hemochrome absorbance (PHA) spectra of Fe(II) MBP-Hm16 (solid line), Az-Hm14 (dashed line), and MP-8 (dotted line). The concentrations calculated for samples of MBP-Hm16, Az-Hm14, and MP-8 using the known $\epsilon_{PHA}$ of 30.27 mM$^{-1}$ cm$^{-1}$ at 550 nm were 2.6 µM, 4.7 µM, and 8.2 µM respectively. The PHA spectra for both MBP-Hm16 and Az-Hm14 show the characteristic 550- and 521-nm bands for c-type heme, indicating proper heme attachment to the CXXCH motif of the peptide tag. The Fe(II) PHA spectrum of MP-8 is shown for comparison.

Figure 10:
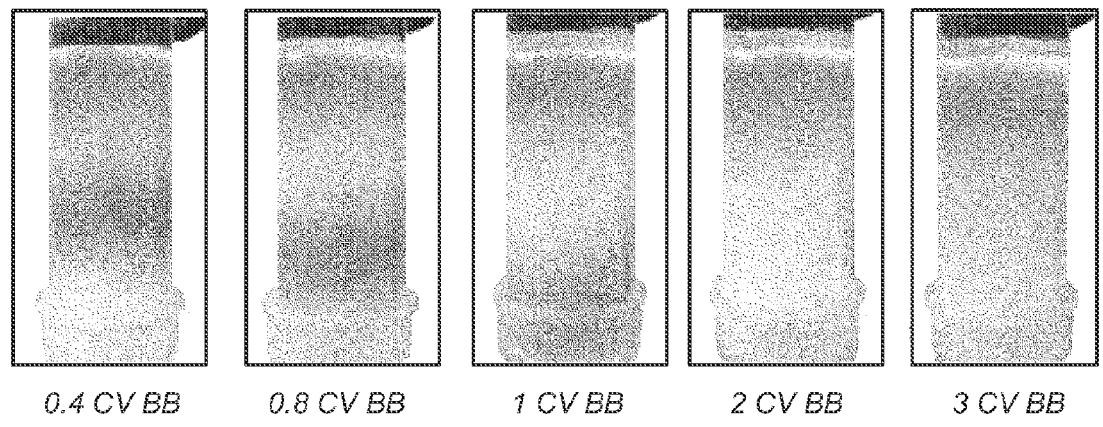

FIG. 10. Photographs of N-terminally tagged azurin bound to the HIS column after several column volumes (CV) of added binding buffer (BB). The affinity for the resin appeared to be higher than the C-terminally tagged variants because there was little detected migration of the bound protein band on the column with added binding buffer for this N-terminally tagged azurin.

Figure 11:
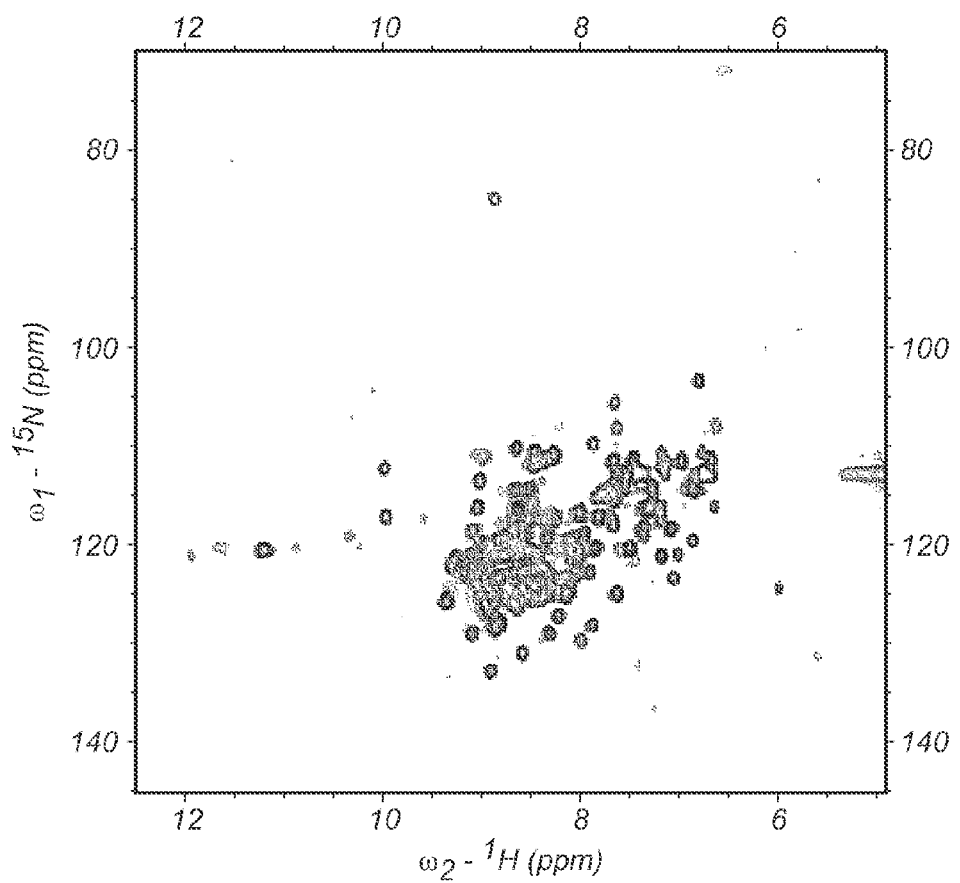

FIG. 11. 500-MHz NMR spectra ($^1$H-$^{15}$N HSQC) of heme-tagged azurin in the presence of imidazole. The peak dispersion shows that the protein is well-folded after heme-tagging.

Figure 12:
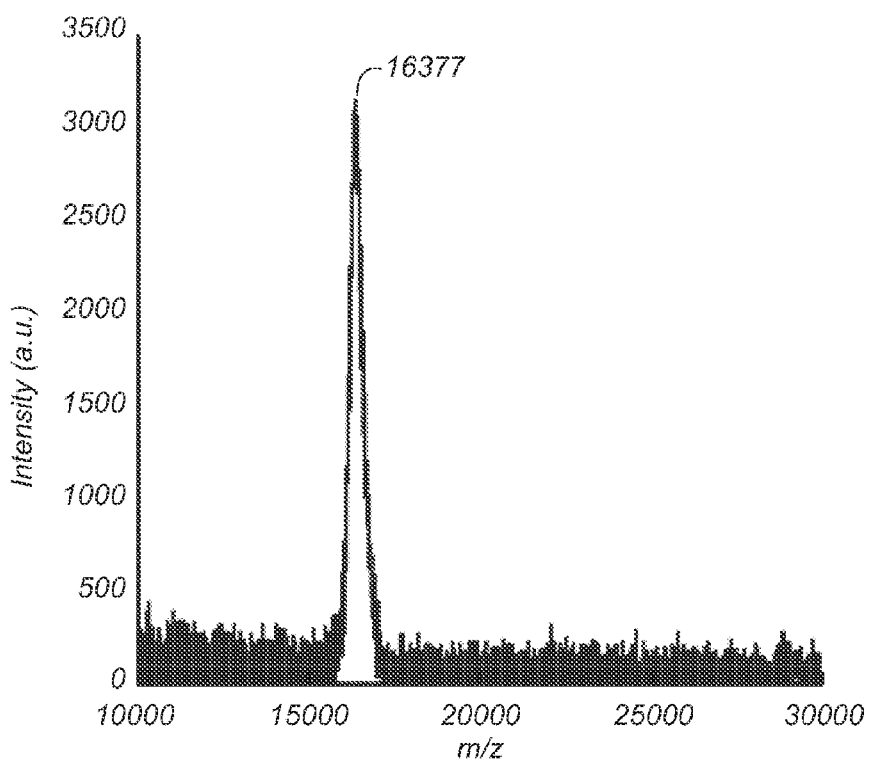

FIG. 12. MALDI-TOF mass spectrum of N-terminally heme tagged azurin.

Figure 13:
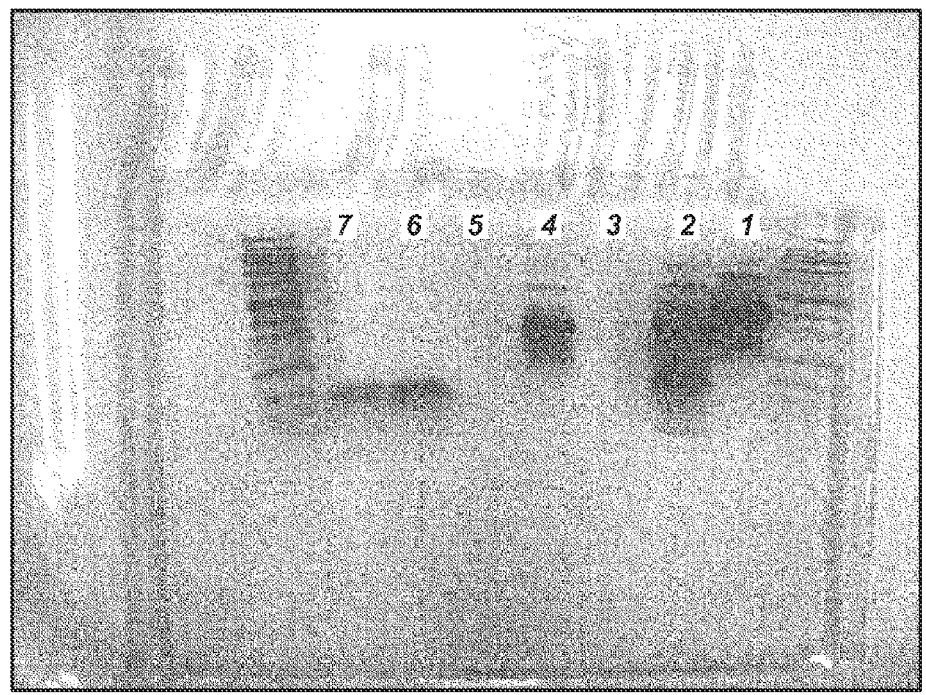

FIG. 13. SDS-PAGE results showing cleavage of heme tag from azurin using the factor Xa endopeptidase. Lane 1: non-cleaved heme-tagged azurin; Lane 2: heme-tagged azurin digested with factor Xa showing cleaved protein and cleaved heme-tagged peptide; Lane 3: blank; lane 4: cleaved (non-tagged) azurin obtained by washing digested protein through the HIS column (HIS column binds cleaved heme tag peptide and does not bind the cleaved non-tagged protein product); Lane 5: Blank; Lane 6 and 7: cleaved heme tag peptide obtained from the HIS column after washing the resin with imidizole.

FIG. 14. Photograph of bacterial pellets containing expressed PDZ3 domain proteins. Left: Pellet containing wild-type PDZ3 domain, not heme tagged (beige color in original experiment). Center: Pellet containing PDZ3 domain tagged with the first 29 residues of horse cytochrome c (red-brown in original experiment). Right: Pellet containing wild-type horse cytochrome c (red-pink in original experiment).

FIGS. 15A-B. Analysis of cellular lyase containing PDZ3 domain tagged with the 29-residue heme tag corresponding to the N-terminus of horse cytochrome c. (A) UV-vis absorption spectrum of bacterial lysate. The spectrum showed that the lysate contained an overexpressed heme protein because of the prominent absorbance bands near 420 (Soret band) and 530 nm (Q bands), typical of heme. (B) The lysate had a dark orange color as expected for heme-containing material.

5. DETAILED DESCRIPTION OF THE INVENTION

An affinity-based protein purification method is provided. In one embodiment, the method can comprise the steps of providing a heme tag with an open coordination site and tagging the recombinant protein of interest with the heme tag. A resin framework is used, wherein a base that binds to heme is immobilized to the resin, and the open coordination site of the heme tag is capable of reversibly binding to the base immobilized to the resin. The base can be, for example, an amine, pyridine, cyanide, or isocyanide or a derivative thereof. The tagged protein is reversibly bound to the resin, then eluted from the resin and quantified. The method enables the tagged protein to be tracked during protein expression or purification, and can be used to identify secretion of a protein to the periplasm or to tag proteins in the cytoplasm.

In a specific embodiment, the purification method uses the coordination of a heme-tag having an open coordination site at the heme iron to an L-histidine immobilized agarose (e.g., SEPHAROSE®)(HIS) resin for purifying proteins expressed in an expression system, e.g., a bacterial expression system (e.g., *Escherichia coli*) or a yeast expression system (e.g., *Saccharomyces cerevisiae*). This approach provides an affinity purification tag visible to the eye, facilitating tracking of the protein. Proteins can be readily purified using the heme tag-HIS method with high yields.

A method for identifying secretion of a protein to the periplasm is also provided. The method comprises the steps of providing a heme tag with an open coordination site and attaching the heme tag with a bacterial cytochrome c maturation apparatus, thereby tagging the protein with the heme tag. Heme-tagging of the protein is indicative of secretion to the periplasm. A method for cytoplasmic tagging of a protein (or peptide) of interest is also provided. The method can comprise the steps of providing a heme tag sequence fused to a protein of interest, wherein the heme tag sequence encodes a peptide that comprises a CXXCH motif (wherein the "CXXCH" motif may have any of the 20 standard amino acids known in the art as residues in the "XX" positions); providing a fusion construct encoding a fusion protein wherein the N-terminal 29 amino acids of mitochondrial cytochrome c are fused to the N-terminus of the protein of interest; and co-expressing the fusion construct and heme lyase gene in an expression system, thereby producing a heme-tagged fusion protein in the cytoplasm.

A peptide fusion system based on a heme tag is also provided. The peptide fusion system can be used for affinity purification, for visual tracking of expressed protein throughout purification, for protein quantitation using absorption spectroscopy, and for estimation of the protein's extinction coefficient at 280 nm ($\epsilon^P_{280}$). The heme tag (also referred to herein as a "heme peptide tag" or "heme fusion tag") is a small peptide tag that binds heme covalently to a protein upon expression in *Escherichia coli* or other suitable expression system and has been used for visual tracking of protein expression and purification (Braun, M., Rubio, I. G. & Thöny-Meyer, L. A heme tag for in vivo synthesis of artificial cytochromes. Appl. Microbiol. Biotechnol. 67, 234-239 (2005)). Heme tags are known in the art, see, e.g., Braun et al. (Braun, M., Rubio, I.G. & Thöny-Meyer, L. A heme tag for in vivo synthesis of artificial cytochromes. Appl. Microbiol. Biotechnol. 67, 234-239 (2005)). The tagging strategy takes advantage of the bacterial heme attachment apparatus for cytochrome c (cyt c) maturation (ccm) in *E. coli* (Ferguson, S.J., Stevens, J.M., Allen, J.W.A. & Robertson, I.B. Cytochrome c assembly: A tale of ever increasing variation and mystery? Biochim Biophys. Acta-Bioenerg. 1777, 980-984 (2008)), which is composed of eight proteins responsible for recognizing and covalently adding the heme vinyl groups to both cysteines of a conserved Cys-X-X-Cys-His (CXXCH) motif of the peptide fusion tag (ccmABCDEFGH) (Allen, J.W.A. & Ferguson, S.J. What is the substrate specificity of the System I cytochrome c biogenesis apparatus? Biochem. Soc. Trans. 34, 150-151 (2006)).

Methods for quantitation of proteins of interest are also provided. The peptide fusion system uses heme coordination chemistry. In one embodiment, the method can comprise tagging proteins and immobilizing them in a framework (resin) of agarose (e.g., SEPHAROSE®). Proteins tagged with five-coordinate heme can reversibly bind L-histidine immobilized to a SEPHAROSE® framework, resulting in a highly pure protein sample after elution. Furthermore, expressed protein can be quantitated using the methods disclosed herein. In one embodiment, the $\epsilon^P_{280}$ is estimated using standard heme quantitation procedures without the need for proteolytically removing the tag.

Also provided are methods for using the heme tag for 1) affinity purification of a protein, 2) visual tracking of a protein during expression and purification, 3) quantitation of a protein using absorption spectroscopy, and 4) determination of a protein's extinction coefficient at 280 nm ($\epsilon_{280}$).

For clarity of disclosure, and not by way of limitation, the detailed description of the invention is divided into the subsections set forth below.

5.1 Heme Tag for a Protein or Peptide of Interest

A heme tag (also referred to herein as a "heme peptide tag" or "heme fusion tag") that can be fused or appended to a protein or peptide of interest is provided. Methods for producing a heme tag fused or appended to a protein or peptide of interest are also provided.

A heme peptide is a heme (iron protoporphyrin IX) covalently bound to a peptide.

A heme tag ("heme peptide tag" or "heme fusion tag") is a heme peptide that can be fused or appended to a protein of interest, thereby tagging the protein or peptide.

In one embodiment, the heme tag comprises a heme covalently bound to a short polypeptide appended to the C-terminus or to the N-terminus of a protein. A heme tag also may be inserted within the protein sequence, in particular in a loop or other region that is solvent exposed and conformationally flexible. The polypeptide is designed to include a CAACH (SEQ ID NO:1), CAQCH (SEQ ID NO:2), CAECH (SEQ ID NO:3) or CWACH (SEQ ID NO:4) (C=cysteine, H=histidine, A=alanine) motif (referred to collectively herein as "CXXCH") that is recognized by the cytochrome c maturation (CCM) apparatus of *E. coli*. In other embodiments, the heme tag "CXXCH" sequence may have any of the 20 standard amino acids as residues in the "XX" positions.

In addition to having a CXXCH segment, the heme tag sequence is preferably designed, using methods known in the art, to have high flexibility and solubility in water to prevent interactions with the protein to which it is attached, e.g., by selecting amino acid residues that have small side chains and/or high polarity. These properties facilitate its use as an affinity tag, and minimize any effects the tag may have on the protein. The heme tag also is also preferably designed to maintain an open coordination site at the heme iron, which will be the affinity site for purification (FIG. 1). In one embodiment, the sequence is: STAGCAACHADSER (SEQ ID NO:5).

5.2 Affinity Purification Column

For design of an affinity purification column for heme-tagged proteins, use is made of heme coordination chemistry, which is well known in the art. The heme tag with an open coordination site at iron (or a weak donor to iron such as water) has affinity for imidazole or histidine (or other bases). In one embodiment, a HIS (HIS=histidine-immobilized agarose, e.g., SEPHAROSE®; FIGS. 2*a-c*) affinity column is used that comprises of L-histidine immobilized to a Sepharose framework. In other embodiments, any resin known in the art that is compatible with proteins can be used, coupled to any base known in the art to bind to heme including amines, pyridines, cyanide, or isocyanide derivatives.

The HIS column has very low affinity for proteins, DNA, lipids, and carbohydrates. In fact, few moieties will have affinity for the HIS column aside from metal ions with open coordination sites. Specificity for the heme-tagged protein is thus very high, which leads to highly purified samples. After allowing the heme-tagged protein to bind to the HIS resin, the protein can be eluted by adding excess imidazole which disrupts the HIS-heme interaction (FIGS. 2*a-c*)

In one embodiment, His-tagged proteins can be bound to the column in phosphate buffer, pH 7, and eluted by adding 200-500 mM imidazole, or binding buffer at pH less than 5 or greater than 8. The HIS column exhibits a low level of non-specific binding of untagged cellular proteins to the affinity medium for the systems studied here. An additional advantage of using the heme tag-HIS method for purification is that the heme tag can be exploited for protein quantitation by using the pyridine hemochrome absorbance method (pyridine hemochrome assay) for heme concentration determination, which is a method well known in the art.

5.3 Visualization of Tagged Protein of Interest

Any standard visualization (e.g., colorimetric) method known in the art can be used to visualize the tagged protein of interest. The intense color of the heme tag allows visualization of the tagged protein of interest throughout purification. An additional benefit of the heme tag is that it acts as a colorimetric indicator of heme-mediated binding to the HIS resin, as it is brown when "5-coordinate" (no additional group bound to iron other than a weak ligand like water) and red/orange when "6-coordinate" (bound to the HIS column or to free imidazole; see demonstration below). This effect is not required for the function but is helpful for monitoring the binding of the protein to the column.

5.4 Protein Purification

The heme tag provided herein can be appended to any protein of interest using the methods disclosed herein. The heme tag can be fused to the N-terminus or the C-terminus of a protein of interest. As a control, a His$_7$ tag can be appended on the C-terminus of a C-terminal heme tag (resulting tag sequence: STAGCAACHADSERHHHHHHH) (SEQ ID NO:6). This can be used, for example, to directly compare the process of and results obtained by using a heme affinity column with the widely used, art known immobilized metal affinity column (IMAC), which is widely used to purify His-tagged proteins. A heme-tagged protein of interest (or a heme-tagged/His-tagged protein of interest) can be expressed in *E. coli* using standard methods. In one embodiment, a second plasmid, pEC86, (Arslan, E., Schulz, H., Zufferey, R., Kunzler, P. & Thöny-Meyer, L. Overproduction of the *Bradyrhizobium japonicum* c-type cytochrome subunits of the cbb(3) oxidase in *Escherichia coli*. Biochem. Biophys. Res. Commun 251, 744-747 (1998)) can be present for overexpression of the cytochrome c maturation factors to facilitate heme attachment. Expression of the heme-tagged protein will yield a dark brown bacterial pellet, consistent with overexpression of heme protein in which the heme has an open coordination site. Expression of heme-tagged/His-tagged protein of interest will yield a pink cellular pellet, consistent with binding of the His tag to the heme iron.

The cellular extract containing the heme-tagged protein can be obtained and partially clarified by chromatography on DEAE Sepharose resin. This is a standard type of "clean-up" step can be used before any affinity chromatography method. The resulting brown-colored sample can be loaded on the HIS column in binding buffer (50 mM NaP$_i$, pH 7.0), resulting in a red band at the top of the HIS medium indicating binding to the column. A distinct green band will separate from the red, and elute with approximately 1 column volume (CV) of binding buffer. The green color of the band is likely due to degraded heme, which is commonly observed with heme protein overexpression and purification. The heme-tagged protein can be eluted with 300 mM imidazole dissolved in binding buffer. SDS-PAGE analysis can be performed to monitor the purification process.

In one embodiment, binding and purification of the heme-tagged protein does not require NaCl or eluting agents for decreasing non-specific binding, which is one of the greatest disadvantages of using the polyhistidine tag (His-tag) affinity purification method the His-tag method.

A His$_7$ tag was appended to the C-terminus of the heme tag (resulting tag sequence: STAGCAACHADSERHHHH-HHH) (SEQ ID NO:6). Heme-tagged protein azurin (AzHm) and heme-tagged/His-tagged azurin (AzHm-His$_7$) was expressed in *E. coli* using standard methods. The second plasmid, pEC86, was present for overexpression of the cytochrome c maturation factors to facilitate heme attachment. Expression of AzHm yielded a dark brown bacterial pellet, consistent with overexpression of heme protein in which the heme has an open coordination site. Expression of AzHm-His$_7$ yielded a pink cellular pellet, consistent with binding of the His tag to the heme iron.

A heme-tagged/His-tagged protein can be purified using a binding buffer, e.g., 25 mM NaP$_i$, 1 M NaCl, 60 mM imidazole to minimize binding of non-His-tagged cellular proteins, whereas heme-tag protein can be loaded to the HIS resin in standard phosphate buffer. High NaCl and/or imidazole concentrations can result in irreversible denaturation of some proteins and an advantage of the heme-tag method is the mild conditions that can be used in comparison.

The following example, using *Pseudomonas aeruginosa* azurin protein as an example of a protein of interest, is illustrative of the above-described general approach for appending a heme tag to a protein of interest. To append a heme tag to the small electron transfer protein *Pseudomonas aeruginosa* azurin (Az), a DNA sequence encoding the heme tag peptide was fused to the 3' end of the Az structural gene.

The cellular extract containing AzHm was obtained and partially clarified by chromatography on DEAE Sepharose resin. The resulting brown-colored sample (FIG. 3a) was loaded on the HIS column in binding buffer (50 mM $NaP_i$, pH 7.0), resulting in a red band at the top of the HIS medium indicating binding to the column (FIG. 3b). A distinct green band separated from the red, and eluted with approximately 1 column volume (CV) of binding buffer (FIG. 3c). The green color of the band was likely due to degraded heme, which is commonly observed with heme protein overexpression and purification. The amount of green band depends on the heme tag sequence, suggesting that optimization using standard methods may reduce the amount of degraded product). For example, designing heme tags with shorter linker regions (i.e., the tag is closer to the protein) will result in less green product. In addition, the protein can be expressed in a lower oxygen environment.

AzHm was eluted with 300 mM imidazole dissolved in binding buffer (FIGS. 3d, e).

SDS-PAGE analysis (FIGS. 5a-b) was performed to monitor the purification process. The high degree of purity of AzHm is indicated by the single strong band in lane 8 (the gel was overloaded in this lane to demonstrate the near lack of impurities even at low levels). The only visible impurity is an extremely faint band of slightly lower molecular mass that we propose to be Az that is not heme-tagged. It may have eluted with AzHm as a dimer or was formed by degradation of the heme tag after purification. Proteins were undetectable after 2 CV of binding buffer (lane 5), exemplifying the low degree of non-specific binding to the HIS column as well as the appreciable affinity of the heme tag for the column. Pure AzHm was shown to bind Cu(II) by addition of $CuSO_4$, indicating that the tag does not interfere with copper binding of Az. Purified AzHm yields as high as 5-7 mg $L^{-1}$ culture were obtained using the HIS column method.

AzHm binding and purification did not require NaCl or eluting agents for decreasing non-specific binding, which is one of the greatest disadvantages of the His-tag method. AzHm-$His_7$ had to be purified using a binding buffer of 25 mM $NaP_i$, 1 M NaCl, 60 mM imidazole to minimize binding of non-His-tagged cellular proteins, whereas AzHm could be loaded to the HIS resin in standard phosphate buffer. High NaCl and/or imidazole concentrations can result in irreversible denaturation of some proteins and an advantage of the heme-tag method is the mild conditions that can be used in comparison.

To investigate binding of heme-tagged protein to the HIS resin, pure Cu(II)-Az, AzHm-$His_7$, horse heart myoglobin, and horse heart cytochrome c were loaded on the HIS column in 50 mM NaPi, pH 7.0. All four proteins had no affinity for the column, eluting after 1 CV of binding buffer. The lack of Cu(II)Az binding verifies that AzHm affinity for the column is specific to the heme-tag, and not the Az protein structure. Heme burial in the hydrophobic interior of myoglobin, a 5-coordinate heme protein, and the saturated coordination shell of cytochrome c and AzHm-$His_7$ heme, apparently prevents binding to the HIS column as expected. These controls indicate that a 5-coordinate, solvent exposed heme tag is required for binding the His column, and also support our proposal that this column will be highly specific for the heme tag. To test the requirement for heme with an open coordination site, MP-8 was loaded on the HIS column in 50 mM $NaP_i$, pH 7.0. MP-8 bound to the top of the column, and was eluted using the same procedures as for AzHm, verifying heme iron-histidine coordination as the mechanism of binding.

5.5 Protein Quantitation and Determination of $\epsilon_{280}$

Methods for using the heme tag to accurately quantitate the amount of tagged protein present and/or to determine the extinction coefficient at 280 nm ($\epsilon_{280}$) for the native untagged protein are provided. Determining $\epsilon_{280}$ is important for measuring the amount of protein present, as is needed in a range of studies and applications, but $\epsilon_{280}$ is notoriously difficult to determine accurately for proteins. The method provided herein can comprise determining the amount of heme-tagged protein present from the spectrum of the heme and correcting for the $\epsilon_{280}$ of the heme tag, yielding $\epsilon_{280}$ for the untagged protein.

In addition to obtaining pure protein using the HIS column method, in another embodiment, the heme tag can be used to quantitate a protein of interest by the pyridine hemochrome absorbance (PHA) method. In this art-known method, the heme-tagged protein is incubated with excess NaOH and pyridine. This forms a bis-pyridine heme that has precisely known extinction coefficients, allowing the heme concentration to be determined using Beer's law (relationship between absorbance, extinction coefficient, and concentration), a standard method known in the art. $\epsilon_{280}$ can also be determined for the protein of interest in the absence of the heme tag.

To obtain $\epsilon_{280}$, the contribution of heme to $\epsilon_{280}$ is preferably determined using microperoxidase-8 (MP-8, a small heme peptide) as a model system for the contribution of absorbance at 280 nm from the heme tag. MP-8 does not contain aromatic residues or disulfide bonds, and has a five-coordinate heme structure, making it a suitable model system as only the heme itself should contribute to $\epsilon_{280}$. To prevent any dimer formation through the open coordination site of MP-8 and the heme-tagged protein, and to minimize any effects of buffer and pH on results, absorption measurements are preferably taken in the presence of excess sodium cyanide which strongly coordinates the heme iron. Using the concentrations of heme tagged protein and MP-8 determined from the PHA, $\epsilon_{280}$(heme-tagged protein-CN) and $\epsilon_{280}$(MP-8-CN) can be determined from the corresponding absorbance values. The UV-Vis spectra of heme-tagged protein-CN and MP-8-CN can be compared, and will be expected to differ at the 280-nm band. $\epsilon_{280}$(protein of interest) is determined by subtracting $\epsilon_{280}$(MP-8-CN) from $\epsilon_{280}$(heme-tagged protein of interest-CN). As an alternative to the PHA method, the extinction coefficients for CN-bound heme tag in the visible region obtained from MP-8-CN may be used to determine the amount of heme-tagged protein present in a sample.

Less preferably, the contribution of heme to $\epsilon_{280}$ can also be determined by other methods known in the art, e.g., the Bradford Assay (staining with Coomassie Brilliant Blue and then relating this value to the absorbance at 280 nm) or the Lowery method.

The following example, using *Pseudomonas aeruginosa* azurin protein as an example of a protein of interest, is illustrative of the above-described general approach for quantitation of a protein of interest. The heme tag was used to quantitate an exemplary protein, AzHm, by the pyridine hemochrome absorbance (PHA) method. The heme concentration was determined using Beer's law. $\epsilon_{280}$ was also determined for Az ($\epsilon_{280}$(Az)) in the absence of the heme tag. To obtain $\epsilon_{280}$(Az), the contribution of heme to $\epsilon_{280}$ was determined using MP-8. Absorption measurements were taken in the presence of excess sodium cyanide which strongly coordinated the heme iron. Using the concentrations of AzHm and MP-8 determined from the PHA, $\epsilon_{280}$(AzHm-CN) of 17.40 mM$^{-1}$cm$^{-1}$ and $\epsilon_{280}$(MP-8-CN) of 9.01 mM$^{-1}$cm$^{-1}$ were determined from the corresponding absorbance values. The UV-Vis spectra of AzHm-CN and MP-8-CN were virtually identical, except for the 280-nm band. $\epsilon_{280}$(Az) was determined by subtracting $\epsilon_{280}$(MP-8-CN) from $\epsilon_{280}$(AzHm-CN), giving 8.39 mM$^{-1}$cm$^{-1}$. Owing to the difficulty of determining this value, reports of $\epsilon_{280}$ (Az) reported in the literature vary, but those most typically used range from 8.5-9.0 for Cu(II), Zn(II), and apo Az.

5.6 Heme-Tagging of Proteins Exported to the Periplasm

The heme fusion tag can be used for affinity-based protein purification that has color for visual tracking. For example, in one embodiment, the heme fusion tag, when attached by the E. coli cytochrome c maturation apparatus in E. coli, can be a colorimetric indicator of transport to periplasm. The heme is attached only if the protein/peptide is exported to periplasm, and a visible change to the color of the cells results. This can serve as an easy assay for researchers wishing to screen for secretion to periplasm.

The bacterial pellets in FIG. 4c shows how the pellet will have an intense color if the protein targeted for the periplasm is successfully transported to the periplasm. If the protein is unsuccessfully transported to the periplasm, the peptide fusion containing the CXXCH motif will not be covalently modified with heme and the pellet will have a typical light tan 'colorless' pellet.

The heme fusion tag can be used to heme-tag proteins that are exported to periplasm via the tat system, which exports folded proteins. The fusion peptide can be located at a terminus of the protein, where it will not interact strongly or fold with the protein.

Any protein that can be expressed in E. coli with a heme-tag sequence and exported to periplasm can potentially be heme-tagged by the E. coli apparatus.

5.7. Heme-Tagging Proteins of Interest in Bacterial Cytoplasm

Some of the embodiments of the heme-tagging method disclosed above can require export of the protein of interest to periplasm for heme-tagging. This step may be a limitation for heme-tagging some proteins, in particular large proteins. Thus, in another embodiment, a method for heme-tagging proteins in the bacterial cytoplasm is provided. Any suitable bacteria known in the art for protein expression (e.g., E. coli) can be used. With cytoplasmic tagging, export to periplasm, which may be a limitation with some proteins, is not required.

Expression of cytochrome c and maturation (heme attachment) in the cytoplasm is known in the art (Pollock et al., Biochemistry 1998, 37, 6124-6131). Cytochrome c can be produced in the bacterial (e.g., E. coli) cytoplasm by co-expressing the cytochrome c structural protein without a signal sequence and with yeast cytochrome c heme lyase. The lyase attaches the heme to the polypeptide in the cytoplasm. This system, however, does not have broad use because the heme lyase has only been shown to attach heme to mitochondrial and select eukaryotic (including horse) cytochrome c, and thus is not expected to attach heme to some heme tag designs.

It is known in the art, however, that mixing a synthetic peptide corresponding to the 25 N-terminal amino acids of horse cytochrome c with yeast mitochondria and hemin (heme) yields peptide with heme covalently attached, indicating that the N-terminal region contains the necessary recognition elements for recognition by heme lyase (and any other unidentified factors facilitating heme attachment) (Veloso et al., J. Biol. Chem. 1984, 259, 6067-6073. Thus, in one embodiment, the N-terminal amino acids of a cytochrome c can be fused to the N-terminus of the target protein and this fusion can be co-expressed in E. coli along with the heme lyase gene. Any mitochondrial cytochrome c known in the art can be used. The N-terminal amino acid sequence is in certain embodiments, 5-10, 10-20, 20-30, 30-50 or longer. In a specific embodiment, the N-terminal sequence of amino acids is 20, 21, 22, 23, 24, 25, 26, 27, 28, 29 or 30 amino acids long. The heme attaches based on recognition of the amino acid N-terminal fusion. This heme-tagged protein can then be subjected to chromatography on the HIS column.

In a specific embodiment, the N-terminal 29 amino acids of horse cytochrome c are fused to the N-terminus of the target protein (PSD95-PDZ3 domain protein, 10 kDa, 93 amino acids):

GDVEKGKKIFVQKCAQCHTVEKGGKHKTG-PDZ3 Domain (SEQ ID NO:7). See Section 6.8 for an example of heme-tagging in the E. coli cytoplasm.

5.8. Additional Embodiments

In one embodiment, the heme tag can be attached to the N-terminus of a protein either in place of or in addition to the C-terminus. In another embodiment, the sequence (length, composition) of the heme tag peptide can be varied to optimize its compatibility with different proteins, its affinity for the HIS column or related columns developed to have affinity for heme, its solubility, its overall charge, or other properties. Variations in the tag sequence also may decrease the amount of heme degradation. In another embodiment, the tag can be readily modified, using methods known in the art, to accommodate a convenient proteolysis site so that it can be cleaved from the protein after use. In addition, the expression vector can be modified so that a unique restriction site is placed at the end of the signal sequence so that any protein can be readily cloned into the site between the signal sequence and the heme tag in one step.

Buffer pH can affect binding to the column. Thus a preferred binding pH range is 6.5-7.5. pH values higher than 8.0 can interfere with binding, which is owing to competing hydroxide coordination of the heme tag. Increasing imidazole concentrations to 200 mM or higher, lowering pH to 5, or increasing the pH above 8 can be used to elute the protein from the column.

Some degradation of the heme tag (manifested as a green degradation product) can occur, owing to the action of heme oxygenases. In preferred embodiments, the following approaches can be used to reduce this degradation and increase the stability of the heme tag:

Limiting aeration of growth can decrease the degradation of heme tag and increase the overall yield. This is achieved by covering incubation flasks with foil, growing in larger volumes of medium, and/or decreasing shaking speed.

Longer tags can show more degradation. In preferred embodiments, finding the shortest heme tag that allows for binding to the HIS column may limit heme degradation.

Adding heme oxygenase inhibitors to the expression medium can also dramatically decrease heme tag degradation. Aeration can be limited by 1) covering the flasks with foil and/or 2) growing in larger volumes.

Making the heme tag more bulky by using a c-heme protein (a cytochrome c) engineered to increase exposure of the heme so that binding to the HIS column is possible is another approach we are interested in pursuing. This can yield greater protection of the tag from degradation (and other reactions) while allowing binding to the HIS column.

The 6-coordinate heme tag shows little degradation. Switching the coordination from 6 to 5 (i.e., through pH control) from a protected to open state can allow one to "turn on" the binding function of the heme only when needed.

In another embodiment, a heme tag sequence can be used that allows HIS column binding while minimizing heme degradation.

Other modifications for preferred embodiments include:

Using ligands other than histidine or imidazole-based ligands for the "HIS" column for affinity purification. In particular, cyanides or isocyanides can have a higher affinity for the heme than histidine. Amines and pyridines can also be used in certain embodiments. A series of columns with different heme affinities can be produced for optimization according to need, or for a multi-step purification to achieve ultra-pure product.

Using proteins tagged with more than one heme in series, which in certain embodiments, offer improvement over the single-heme-tagged variants. Multi-heme tagged variants can have higher affinity for the HIS column.

5.9. Uses of the Heme Fusion Tag

The heme fusion tag can be used both for affinity purification and protein quantitation. It offers multiple methods for elution (imidazole, or an adjustment of pH of the buffer up or down). It results in highly pure samples, for example, samples that are purer protein than the popular His-tag. The heme tag can also be loaded onto the HIS column for purification under mild conditions, which is not the case for the His-tag. Thus proteins that are unstable in high salt can be purified using the heme tag but not the His-tag.

The heme tag allows expressed protein purification in a small number of steps (lysis, clarification, HIS column) and allows one to visually track protein purification. The heme-tag/HIS method gives highly pure protein (in our initial tests), with higher purity than one obtains with the His-tag/IMAC procedure. It also allows the protein to be exposed to mild conditions throughout the procedure, i.e., there is no need for use of high salt which is required for His-tag operation. The heme tag provides a means by which to accurately quantitate protein, which is a major problem, as existing methods are unsatisfactory.

According to the methods disclosed herein, a small peptide fusion tag that binds heme covalently can be used for visual tracking of protein expression, one step affinity purification, and for quantitating protein. The heme fusion tag can be used in the development of an immobilized histidine column (HIS) for affinity purification of heme-tagged proteins, 2) the development of a particular heme-tag sequence that binds to the HIS column, and 3) the use of the heme tag for protein extinction coefficient determination.

Fusion tags for proteins exist for a variety of applications, including affinity purification, solubility enhancement, and protein detection. There is a need in the art for development of new fusions, particularly those with multi-functional applications. The methods provided herein offer visual tracking and affinity purification in one tag. It allows for operation under milder conditions and yields better results than the very popular protein affinity purification tag, the His-tag.

Additional details of the above described embodiments are set forth in the following Examples. The Examples are offered by way of illustration and not by way of limitation.

6. EXAMPLES

6.1. Example 1

Use of a Heme Fusion Tag for Protein Purification and Quantitation

6.1.1. Introduction

This example demonstrates a peptide fusion system based on the heme tag developed by Thöny-Meyer and coworkers (Braun, M., Rubio, I.G. & Thöny-Meyer, L. A heme tag for in vivo synthesis of artificial cytochromes. Appl. Microbiol. Biotechnol. 67, 234-239 (2005)) that can be used for affinity purification, visual tracking of expressed protein throughout purification, protein quantitation using absorption spectroscopy, and estimation of the protein's extinction coefficient at 280 nm ($\epsilon^P_{280}$). The heme tag is a small peptide fusion tag that binds heme covalently to a protein upon expression in *Escherichia coli* and has been used for visual tracking of protein expression and purification. (Braun M, Rubio IG, Thony-Meyer L (2005) A heme tag for in vivo synthesis of artificial cytochromes. Appl. Microbiol. Biotechnol. 67: 234-239). This tagging strategy takes advantage of the bacterial cytochrome c (cyt c) maturation (ccm) apparatus in *E. coli*, (Kranz RG, Richard-Fogal C, Taylor JS, Frawley ER (2009) Cytochrome c biogenesis: mechanisms for covalent modifications and trafficking of heme and for heme-iron redox control. Microbiol. Mol. Biol. Rev. 73: 510-528) which covalently adds the cysteines of a conserved Cys-X-X-Cys-His (CXXCH) motif to the two heme vinyl groups (Allen JWA, Ferguson SJ (2006) What is the substrate specificity of the System I cytochrome c biogenesis apparatus? Biochem. Soc. Trans. 34: 150-151).

The ccm system is comprised of eight integral membrane proteins (ccmABCDEFGH) that face the periplasmic side of the cytoplasmic membrane (Kranz RG, Richard-Fogal C, Taylor JS, Frawley ER (2009) Cytochrome c biogenesis: mechanisms for covalent modifications and trafficking of heme and for heme-iron redox control. Microbiol. Mol. Biol. Rev. 73: 510-528). Thus, proteins carrying the peptide fusion must contain an amino-terminal signal sequence for translocation to the periplasmic space for covalent heme attachment (Braun M, Rubio IG, Thony-Meyer L (2005) A heme tag for in vivo synthesis of artificial cytochromes. Appl. Microbiol. Biotechnol. 67: 234-239). A complete understanding of the mechanism by which the cofactor is attached to the CXXCH motif by the ccm system is an active area of research (Kranz RG, Richard-Fogal C, Taylor JS, Frawley ER (2009) Cytochrome c biogenesis: mechanisms for covalent modifications and trafficking of heme and for heme-iron redox control. Microbiol. Mol. Biol. Rev. 73: 510-528). However, it has been shown that recognition for heme attachment depends on the presence of a CXXCH motif (Allen JWA, Ferguson SJ (2006) What is the substrate specificity of the System I cytochrome c biogenesis apparatus? Biochem. Soc. Trans. 34: 150-151).

The example demonstrates the use of heme coordination chemistry and demonstrates that proteins tagged with five-coordinate heme will reversibly bind L-histidine immobilized to a Sepharose framework, resulting in a highly pure protein sample after elution. Furthermore, we quantitate expressed protein and estimate the $\epsilon^P_{280}$ using standard heme quantitation procedures without the need for proteolytically removing the tag.

6.1.2. Heme Tag Design, Fusion Plasmid Construction and Protein Expression

It is known in the art that heme tags can be developed having both six- and five-coordination at the heme iron (Braun, M., Rubio, I.G. & Thöny-Meyer, L. A heme tag for in vivo synthesis of artificial cytochromes. Appl. Microbiol. Biotechnol. 67, 234-239 (2005)). The porphyrin provides four coordinating atoms through its pyrrole nitrogens, and the heme-binding CXXCH sequence supplies the His that occupies the fifth site. Tags that have a polyhistidine sequence (His-tag) near the CXXCH motif yield a six-coordinate heme iron, with one of the His residues occupying the axial binding site to heme. The absence of the His-tag allows for a five-coordinate heme with an open site at iron available to bind exogenous ligands. For an N-terminal tag, a HHHHHH (SEQ ID NO:8) sequence on the N-terminal side of the tag may bind the heme.

The model proteins used in this example were the blue copper protein *Pseudomonas aeruginosa* azurin (Az) and *E. coli* maltose binding protein (MBP). Table 1 lists the heme-tagged Az and MBP variants prepared in this example with their corresponding peptide fusion tag sequences and expected heme coordination. The commercial MBP construct used includes a carboxyl-terminal 12-amino acid spacer to which the amino terminus of the Hm16 tag was connected. The heme tags of the Az variants are directly attached to the protein carboxyl terminus.

TABLE 1

Heme-tagged fusion proteins with corresponding tag amino acid sequences and heme-iron coordination.

| Protein Fusions[a] | Heme-Tag Peptide Sequence[b] | Heme-Iron Coordination |
|---|---|---|
| Az-Hm14 | GATS<u>CAACH</u>ADSER (SEQ ID NO: 9) | Five |
| Az-Hm20 | GATS<u>CAACH</u>ADSEHHHHHHH (SEQ ID NO: 10) | Six |
| MBP-Hm16 | IEGREAT<u>CAQCH</u>ATAD (SEQ ID NO: 11) | Five |
| Az-MP301 | NSRYPAA<u>CLACH</u>AIG[c] (SEQ ID NO: 12) | Five |

[a]The heme tags developed in this example are abbreviated as Hm followed by the number of amino acids in the peptide. The MP301 tag was previously described.
[b]The heme attachment motifs are underlined.
[c]Reported in Braun, M., Rubio, I.G. & Thöny-Meyer, L. A heme tag for in vivo synthesis of artificial cytochromes. Appl. Microbiol. Biotechnol. 67, 234-239 (2005).

Expression vectors were constructed to express each variant with a carboxyl-terminal heme tag (FIGS. 4a-b and Section 6.1.7). The five-coordinate heme tags of Az-Hm14 and MBP-Hm16 are provided herein, while that of Az-MP301 was previously described (Braun, M., Rubio, I.G. & Thöny-Meyer, L. A heme tag for in vivo synthesis of artificial cytochromes. Appl. Microbiol. Biotechnol. 67, 234-239 (2005)). The expression vectors and the pEC86 (Arslan E, Schulz H, Zufferey R, Kunzler P, Thony-Meyer L (1998) Overproduction of the *Bradyrhizobium japonicum* c-type cytochrome subunits of the cbb3 oxidase in *Escherichia coli*. Biochem. Biophys. Res. Commun. 251: 744-747) plasmid carrying the ccm gene array were cotransformed in *E. coli* for protein overexpression. For the five-coordinate heme tag designs (Hm14 and Hm16), polar amino acids were included to enhance water solubility. A six-coordinate His-tagged variant of Az-Hm14 (Az-Hm20) with seven histidines was prepared for comparison (Section 6.1.7). The bacterial pellets containing Az-Hm14, MBP-Hm16, and Az-MP301 were dark brown in color, and pellets containing Az-Hm20 exhibited a red color, consistent with overexpression of five- and six-coordinate heme proteins, respectively (FIG. 4c).

6.1.3. Purification of Az-Hm14 and MBP-Hm16

The ability of five-coordinate heme to reversibly bind exogenous ligands suggests that the heme tag could be exploited for affinity-based purification. A Sepharose resin was prepared that contains the amino acid L-histidine covalently coupled by a 10-atom spacer to immobilize the heme-tagged proteins. Histidine was chosen because it is a common heme ligand and is not expected to bind or react with most other biological molecules to any appreciable extent. Partially clarified cytoplasmic brown-colored cell extract containing Az-Hm14 was loaded on the L-histidine immobilized Sepharose (HIS) resin equilibrated in 50 mM sodium phosphate ($NaP_i$), resulting in a red band at the top of the medium when washed with the same buffer (FIG. 5c). The red color suggests coordination of histidine to heme iron. A distinct green band separated from the red and eluted with approximately 1-1.3 column volumes (CV) of binding buffer. The green color of the band was likely due to the presence of degraded heme from activity of *E. coli* heme oxygenases (Suits, M.D.L., Jaffer, N. & Jia, Z.C. Structure of the *Escherichia coli* 0157: H7 heme oxygenase ChuS in complex with heme and enzymatic inactivation by mutation of the heme coordinating residue His-193. J. Biol. Chem. 281, 36776-36782 (2006)).

The effect of buffering species and pH was investigated, with 50 mM $NaP_i$ buffer at pH values of 6.5 to 7.5 identified to be optimal for binding. Tris-HCl buffer, which coordinates with metals, interfered with Az-Hm14 binding to the HIS resin. Binding buffer containing 200-500 mM imidazole, binding buffer at a pH below 5, or at a pH above 8 was found to elute Az-Hm14 from the HIS resin (FIG. 5c). Binding buffer at pH 5 results in the histidines of the resin being protonated and unavailable to coordinate heme iron, while at pH 8 we propose that hydroxide ions compete as ligands to heme iron. Crude periplasmic extract containing MBP-Hm16 behaved similarly when loaded on the HIS resin using the same buffer conditions as described for Az-Hm14 (FIG. 6c). MBP-Hm16 was eluted using binding buffer supplemented with imidazole as described for Az-Hm14. Clarified cytoplasmic extract containing Az-MP301 (prepared as described for Az-Hm14) remained brown in color with the addition of binding buffer when loaded on the HIS resin. The brown band eluted with approximately 1.0 CV of binding buffer, indicating that the protein did not bind the HIS resin.

Purity of the Az-Hm14 and MBP-Hm16 samples was assessed by SDS-PAGE of fractions taken during the purification process. The fraction containing red protein eluted using imidazole yielded a single band at molecular weight~15 kDa for Az-Hm14 (lane 8, FIG. 5a) and a single band at ~45 kDa for MBP-Hm16 (lane 1, FIG. 6a) visualized using both Coomassie and heme stain (Section 6.1.7). A comparison of the crude cellular lysate containing Az-Hm14 before and after partial clarification is shown in lanes 2 and 3 of FIG. 5a, showing no significant protein purity difference. Lane 4 of FIG. 6a is the crude periplasmic extract containing MBP-Hm16. The results of elution of binding buffer after loading heme-tagged proteins are shown in lanes 4 and 5 of FIG. 5a for Az-Hm14 purification and lane 3 of FIG. 6a for MBP-Hm16 purification. The proteins that elute at 0.9 CV of binding buffer are visualized in lane 4 (FIG. 5a) for Az-Hm14 purification, and lane 3 (FIG. 6a) for MBP-Hm16 purification. The UV-vis spectra of Az-Hm14 (FIG. 5b) and MBP-Hm16 (FIG. 6b) in 50 mM $NaP_i$, pH 7.0 purified using the HIS resin show a Soret band at 401 and 398 nm respectively, values consistent with five-coordinate microperoxidases (Lombardi, A., Nastri, F. & Pavone, V. Peptide-based heme-protein models. Chem. Rev. 101, 3165-3189 (2001)). Purified Az-Hm14 and MBP-Hm16 yields of 7 and 0.8 mg per L culture, respectively, were obtained using the HIS column method. MBP-Hm16 yield was lower than that of Az-Hm14 due to the difference in expression vector and a higher level of degradation of the heme cofactor.

Az-Hm14 and MBP-Hm16 were further characterized after purification by exploiting their abilities to bind native ligands/metals. Az is a copper-binding protein that exhibits a distinct blue color due to a Cys(S)-to-Cu(II) charge transfer band at 625 nm upon coordinating Cu(II) (Mizoguchi, T.J., DiBilio, A.J., Gray, H.B. & Richards, J.H. Blue to Type-2 Binding: Copper(II) and cobalt(II) derivatives of a Cys112Asp mutant of Pseudomonas aeruginosa azurin. J. Am. Chem. Soc. 112, 10076-10078 (1992)). MBP is widely used as an affinity fusion tag that binds immobilized amylose resins and maltose (Srinivasan, U. & Bell, J.A. A convenient method for affinity purification of maltose binding protein fusions. J. Biotechnol. 62, 163-167 (1998)). Pure Az-Hm14 was shown to bind Cu(II) after the addition of $CuSO_4$ by monitoring the appearance of the charge-transfer band at 625 nm (FIGS. 7a-b).

As expected, the solution containing Az-Hm14 exhibited a color change from red to brown due to the blue color exhibited by Cu(II)Az. To test the ligand-binding properties of MBP-Hm16, crude periplasmic extract containing MBP-Hm16 was loaded on amylose resin. MBP-Hm16 formed a band at the top of the column, and eluted after the addition of maltose, confirming that the protein retained the ability to bind amylose and maltose (FIGS. 8a-b).

FIGS. 8a-b show protein purification using amylose resin. To verify that MBP-Hm16 retains its native ligand binding ability, and to compare purification using amylose with the HIS method, the protein was purified using an amylose resin. (a) Photograph of loading crude periplasm containing MBP-Hm16 on amylose resin. A distinct brown/green band formed on the top of the resin, and was washed with 12 CV of the recommended binding buffer to purify. The band eluted after the addition of 10 mM maltose dissolved in binding buffer. (b) Full-length 10% SDS PAGE gel developed with Coomassie stain shown in FIG. 6d. Lane 1: blank, 2 and 4: MBP-Hm16 purified using the HIS column after being partially clarified using an amylose resin, 3: blank, 5: blank, 6: Fraction taken from HIS column after addition of 1.3 column volume (CV) of binding buffer, 7: Fraction taken from HIS column after addition of 0.9 CV of binding buffer 8: Periplasmic extract purified using amylose resin, 9: Purified MBP (New England Biolabs), MW: Molecular weight marker. As is evident by lane 8, the MBP-amylose affinity method for purifying MBP fusions leaves a substantial amount of impurities. These impurities were easily removed by a second round of purification using the HIS resin, with the elution profile of the contaminating proteins shown in lanes 6 and 7. The MBP-Hm16 visible in lanes 6 and 7 that elutes from the HIS resin before the addition of the imidazole is due the presence of degraded heme as revealed by the UV-vis spectrum and green color. Only MBP-Hm16 with non-degraded heme will bind the HIS resin.

After elution from the amylose resin, MBP-Hm16 was loaded onto the HIS medium and a red band formed at the top of the column, confirming that the MBP-Hm16 has affinity for both types of media (FIGS. 8a-b).

To verify the mode of HIS medium binding, pure Cu(II)-Az, Az-Hm20, horse heart myoglobin, and horse heart cytochrome c were each loaded on the HIS column in 50 mM $NaP_i$, pH 7.0 (Section 6.1.7). Each of the four proteins eluted within 1 CV of binding buffer, indicating no appreciable affinity for the HIS resin. The lack of Cu(II)Az binding verifies that Az-Hm14 affinity for the column is specific to the heme tag, and not the Az protein structure. Heme burial in the hydrophobic interior of myoglobin, a five-coordinate b-type heme protein, and the saturated coordination shell of cytochrome c and Az-Hm20 heme presumably prevent binding to the HIS column. These control experiments indicate that a five-coordinate, solvent exposed heme is required for binding the HIS column. To test this requirement, microperoxidase-8 (MP-8), a small five-coordinate heme peptide (Marques, H. M. Insights into porphyrin chemistry provided by the microperoxidases, the haempeptides derived from cytochrome c. Dalton Trans., 4371-4385 (2007)), was loaded on the HIS resin in 50 mM $NaP_i$, pH 7.0. MP-8 bound to the top of the column and was eluted using the same procedures as for the heme-tagged proteins, verifying heme iron-histidine coordination as the mechanism of binding (FIGS. 5a-c)

MP-8 can be prepared using methods known in the art (Low, D. W., Gray, H. B. & Duus, J. Ø. Paramagnetic NMR spectroscopy of microperoxidase-8. Journal of the American Chemical Society 119, 1-5 (1997).

To compare the HIS purification method with commercial affinity purification procedures, Az-Hm20 was purified using the His-tag-IMAC (immobilized metal affinity chromatography) method, and MBP-Hm16 was purified using the MBP-amylose method. Both purification methods were carried out as described by the manufacturers' protocol (Section 6.1.7). As shown in FIG. 5a, contaminants are visible for the Az-Hm20 purification using the IMAC procedure (lane 7), while Az-Hm14 purified on the HIS column appears to be contaminant-free (lane 8); however, the purity difference is not substantial. Significantly greater contamination by E. coli proteins after purification of MBP-Hm16 was observed using the amylose purification method (lane 2, FIG. 6d) than with the HIS method (lane 1, FIG. 6a). Additionally, a second round of purification of MBP-Hm16 using the HIS resin (after purification on amylose resin) removed some of these contaminating protein (lane 1, FIG. 6d), and resulted in a final purity similar to that using the HIS method alone (compare lane 1, FIG. 6a and FIG. 8b).

6.1.4. Quantitation of Heme-Tagged Proteins

The absorption properties of the heme tag were used to quantitate the protein and to determine $\epsilon^P_{280}$ for non-tagged Az and MBP. The concentrations of heme present in the sample was determined using the pyridine hemochrome absorbance (PHA) method which relies on the known extinction coefficient for c-type heme in the presence of excess sodium hydroxide and pyridine ($\epsilon_{PHA}$) (Berry, E.A. & Trumpower, B.L. Simultaneous determination of hemes-a, hemes-b, and hemes-c from pyridine hemochrome spectra. Anal. Biochem. 161, 1-15 (1987)). This value can be used to calculate the concentration of proteins carrying c-type heme, as it has been shown to be independent of the polypeptide chain (Berry, E.A. & Trumpower, B.L. Simultaneous determination of hemes-a, hemes-b, and hemes-c from pyridine hemochrome spectra. Anal. Biochem. 161, 1-15 (1987)).

Az-Hm14 and MBP-Hm16 Fe(II) PHA spectra gave the characteristic 550- and 521-nm bands in the visible region, indicating proper incorporation of c-type heme to the tag (FIG. 9). To obtain $\epsilon^P_{280}$ using the heme tag, the contribution of heme to $\epsilon_{280}$ ($\epsilon^H_{280}$) must be subtracted from that of the heme-tagged proteins ($\epsilon^{PH}_{280}$). The value of $\epsilon^H_{280}$ was determined (9.82 $mM^{-1}$ $cm^{-1}$) using microperoxidase-8 (MP8) as a model system for heme-only absorbance at 280 nm MP8 is a heme peptide from horse cytochrome c corresponding to residues 14-21 with heme bound covalently. It does not contain aromatic residues or disulfide bonds and has a five-coordinate heme structure, making it a suitable model system (Marques, H.M. Insights into porphyrin chemistry provided by the microperoxidases, the haempeptides derived from cytochrome c. Dalton Trans., 4371-4385 (2007)). To prevent dimer formation and to reduce the effects of buffer and pH on results, absorption measurements were taken in the presence of excess sodium cyanide, which strongly binds the open coordination site of the heme iron. Using the concentrations of heme-tagged proteins and MP-8 determined from $\epsilon_{PHA}$, $\epsilon^{PH}_{280}$ for Az-Hm14, MBP-Hm16, and MP-8 in the presence of CN$^-$ were determined from the corresponding absorbance values in NaP$_i$, pH 7.0. To determine $\epsilon^P_{280}$ for Az and MBP, $\epsilon^H_{280}$ was subtracted from $\epsilon^{PH}_{280}$ for the corresponding heme-tagged proteins. Table 2 shows the results of these calculations compared with a range of reported literature values of $\epsilon^P_{280}$ for Az (Vandekamp, M., Hali, F.C., Rosato, N., Agro, A.F. & Canters, G.W. Purification and characterization of a nonreconstitutable azurin, obtained by heterologous expression of the Pseudomonas aeruginosa azu gene in Escherichia coli. Biochim Biophys. Acta 1019, 283-292 (1990); Pozdnyakova, I., Guidry, J. & Wittung-Stafshede, P. Studies of Pseudomonas aeruginosa azurin mutants: Cavities in beta-barrel do not affect refolding speed. Biophys. J. 82, 2645-2651 (2002); Naro, F. et al. Metal binding to Pseudomonas aeruginosa azurin: a kinetic investigation. Z. Naturforsch. (C) 55, 347-354 (2000)) and MBP (Raghava, S., Aquil, S., Bhattacharyya, S., Varadarajan, R. & Gupta, M.N. Strategy for purifying maltose binding protein fusion proteins by affinity precipitation. J. Chromatogr. A 1194, 90-95 (2008); Gilardi, G., Mei, G., Rosato, N., Agro, A.F. & Cass, A.E.G. Spectroscopic properties of an engineered maltose binding protein. Protein Eng. 10, 479-486 (1997); Medintz, I.L., Goldman, E.R., Lassman, M.E. & Mauro, J.M.A fluorescence resonance energy transfer sensor based on maltose binding protein. Bioconjugate Chem. 14, 909-918 (2003)).

TABLE 2

Values for $\epsilon^P_{280}$ for Az and MBP determined using the heme tag variants Az-Hm14-CN and MBP-Hm16-CN.

| | $\epsilon^P_{280}$ (mM$^{-1}$ cm$^{-1}$) | |
|---|---|---|
| Sample | Measured[a] | Reported[b] |
| Az-Hm14-CN | 20.04 | — |
| MBP-Hm16-CN | 90.79 | — |
| MP-8-CN | 9.821 | — |
| Az | 10.22 | 5.9-9.8[c] |
| MBP | 80.93 | 61-77.6[d] |

[a]Measured values were determined in this example using the PHA.
[b]Reported values from the literature were determined by various methods, including experimental and/or predictive methods based on amino acid sequence values used to calculate the $\epsilon^P_{280}$.
[c]Derived from references: Pozdnyakova, I., Guidry, J. & Wittung-Stafshede, P. Studies of Pseudomonas aeruginosa azurin mutants: Cavities in beta-barrel do not affect refolding speed. Biophys. J. 82, 2645-2651 (2002); Naro, F. et al. Metal binding to Pseudomonas aeruginosa azurin: a kinetic investigation. Z. Naturforsch. (C) 55, 347-354 (2000); and Raghava, S., Aquil, S., Bhattacharyya, S., Varadarajan, R. & Gupta, M. N. Strategy for purifying maltose binding protein fusion proteins by affinity precipitation. J. Chromatogr. A 1194, 90-95 (2008).
[d]Derived from references: Gilardi, G., Mei, G., Rosato, N., Agro, A. F. & Cass, A. E. G. Spectroscopic properties of an engineered maltose binding protein. Protein Eng. 10, 479-486 (1997); Medintz, I. L., Goldman, E. R., Lassman, M. E. & Mauro, J. M. A fluorescence resonance energy transfer sensor based on maltose binding protein. Bioconjugate Chem. 14, 909-918 (2003); and Bornhorst, J. A. & Falke, J. J. Purification of proteins using polyhistidine affinity tags. in Applications of Chimeric Genes and Hybrid Proteins, Pt A, Vol. 326 245-254 (Academic Press Inc, San Diego, 2000).

6.1.5. Discussion

This example demonstrates that the heme tags reported here can simultaneously serve as an affinity tag for protein purification, for visual tracking of the protein fusion throughout expression and purification, and for protein quantitation and estimation of $\epsilon^P_{280}$. As an affinity purification tag, the heme tag gives highly favorable results. Non-specific adsorption of cellular proteins to affinity resins is reported with many commonly used purification procedures (Terpe, K. Overview of tag protein fusions: from molecular and biochemical fundamentals to commercial systems. Appl. Microbiol. Biotechnol. 60, 523-533 (2003); Nilsson, J., Stahl, S., Lundeberg, J., Uhlen, M. & Nygren, P.A. Affinity fusion strategies for detection, purification, and immobilization of recombinant proteins. Protein Expr. Purif. 11, 1-16 (1997); Arnau, J., Lauritzen, C., Petersen, G.E. & Pedersen, J. Current strategies for the use of affinity tags and tag removal for the purification of recombinant proteins. Protein Expr. Purif. 48, 1-13 (2006)). The HIS resin described in this example exhibits a low degree of non-specific binding, circumventing the need for supplementing the binding buffer with high concentrations of salts or eluting agents, thus simplifying the purification procedure and allowing for mild column loading conditions.

This is exemplified by comparing the purification of Az-Hm14 using the above-disclosed method with that of Az-Hm20 by the IMAC method. Az-Hm20 was purified using an optimized binding buffer of 25 mM NaP$_i$ pH 7.8 in addition to 1 M NaCl and 60 mM imidazole to minimize nonspecific binding of cellular proteins to the affinity matrix. The concentrations of both NaCl and imidazole in the binding buffer necessary for obtaining pure protein can vary for the IMAC method (Terpe, K. Overview of tag protein fusions: from molecular and biochemical fundamentals to commercial systems. Appl. Microbiol. Biotechnol. 60, 523-533 (2003); Bornhorst, J.A. & Falke, J.J. Purification of proteins using polyhistidine affinity tags. in Applications of Chimeric Genes and Hybrid Proteins, Pt A, Vol. 326 245-254 (Academic Press Inc, San Diego, 2000)), and must be optimized. Even after optimization, some undesired binding of non-tagged E. coli proteins to the IMAC column was observed. The poor purity obtained when using MBP as an affinity tag with the amylose resin has been documented, and recently His-tagged MBP fusions were introduced to gain a higher degree of purity by using affinity purification by IMAC while exploiting the solubility enhancing properties of MBP (Nallamsetty, S. & Waugh, D.S. A generic protocol for the expression and purification of recombinant proteins in Escherichia coli using a combinatorial His(6)-maltose binding protein fusion tag. Nat. Protoc. 2, 383-391 (2007)). The low non-specific binding of proteins to the HIS resin suggests that this method could also find wide application in combination with other existing fusion tags that enhance solubility and increase overall yield.

The lack of binding to the HIS resin by the Az-MP301 variant suggests that the amino-acid composition of the heme tag plays a role in determining efficiency of binding. The MP301 heme tag contains a proline residue in the linker, and Braun et al. suggest that this residue may aid in the recognition of the heme attachment motif by the ccm apparatus (Braun, M., Rubio, I.G. & Thöny-Meyer, L. A heme tag for in vivo synthesis of artificial cytochromes. Appl. Microbiol. Biotechnol. 67, 234-239 (2005)). Proline residues in proteins have the most restricted rotational freedom of any other amino acid (Branden, C. & Tooze, J. Introduction to Protein Structure, 356-357 (Garland New York 1999)), making it possible that the MP301 tag is locked into an unfavorable orientation for binding the HIS resin. Conversely, all of our tag designs include glycine in the linker, an amino acid that can access the widest range of rotational space available compared to the other amino acids (Branden, C. & Tooze, J. Introduction to Protein Structure, 356-357 (Garland New York 1999)). Thus, choosing glycine in combination with polar amino acids for the heme tag linker may be necessary for proper binding to the HIS resin. The tags presented here were all appended to the carboxyl terminus of the proteins. Amino-terminal tags can be constructed in a similar manner.

Purification yields obtained for Az-Hm14 using the HIS method in this example are similar to or higher than those reported for several of the commonly used affinity purification methods. For example, typical yields reported for glutathione S-transferase, intein-chitin binding domain, and the biotin carboxyl carrier protein affinity methods are 10, 0.5-5, and 1-5 mg per L of bacterial culture, respectively (Kimple, M.E. & Sondek, J. Overview of affinity tags for protein purification. in Curr. Protoc. Protein Sci. (eds. Coligan, J.E., Dunn, B.M., Speicher, D.W., Wingfield, P.T. & Ploegh, H.L.) 9.9.1-9.9.19 (John Wiley & Sons, Inc., New York, 2004)). Although MBP-Hm16 yields are lower than Az-Hm14, they fall within this range. The yields we report for AzHm-14 are similar to those of several cyts c overexpressed in *E. coli*, with the latter having a range of 1-12 mg per L, respectively (Russell BS, Zhong L, Bigotti MG, Cutruzzola F, Bren KL (2003) Backbone dynamics and hydrogen exchange of *Pseudomonas aeruginosa* ferricytochrome c551. J. Biol. Inorg. Chem. 8: 156-166; Kellogg JA, Bren KL (2002) Characterization of recombinant horse cytochrome c synthesized with the assistance of *Escherichia coli* cytochrome c maturation factors. Biochim Biophys. Acta 1601: 215-221; Fee JA, Chen Y, Todaro TR, Bren KL, Patel KM, Hill MG, Gomez-Moran E, Loehr TM, Ai JY, Thony-Meyer L, Williams PA, Stura E, Sridhar V, McRee DE (2000) Integrity of *Thermus thermophilus* cytochrome c552 synthesized by *Escherichia coli* cells expressing the host-specific cytochrome c maturation genes, ccmABCDEFGH: biochemical, spectral, and structural characterization of the recombinant protein. Protein Sci. 9: 2074-2084.)

The extent of heme attachment to the CXXCH motif has been shown not to depend on the amount of apo-protein having a heme binding motif in the periplasm (Allen JWA, Barker PD, Ferguson SJ (2003) A cytochrome b562 variant with a c-type cytochrome CXXCH heme-binding motif as a probe of the *Escherichia coli* cytochrome c maturation system. J. Biol. Chem. 278: 52075-52083). To explain this observation, it has been suggested that the availability of free heme transported to the periplasm by an unknown mechanism may determine the yield of protein modified with heme (Allen JWA, Barker PD, Ferguson SJ (2003) A cytochrome b562 variant with a c-type cytochrome CXXCH heme-binding motif as a probe of the *Escherichia coli* cytochrome c maturation system. J. Biol. Chem. 278: 52075-52083). Thus, it is expected that the maximum yield of pure protein obtainable using the heme tag-HIS method will be similar to that of the cyts c currently reported, which we demonstrate with Az-Hm14. This suggests that the yield of high expression proteins (higher than the availability of heme) will be lowered when heme tagged. However, the yields we obtain for heme-tagged proteins in this example, and those obtained for cyts c reported in the literature are sufficient for extensive biophysical characterization.

Protein concentration determination is frequently employed during the purification process. Many procedures exist for protein quantitation, with all having their specific advantages and limitations (Olson, B. J.S.C. & Markwell, J. Assays for determination of protein concentration. in Curr. Protoc. Protein Sci. (eds. Coligan, J.E., Dunn, B.M., Speicher, D.W., Wingfield, P.T. & Ploegh, H.L.) 3.4.1-3.4.29 (John Wiley & Sons, Inc., New York, 2007); Stoscheck, C.M. Quantitation of proteins. Methods Enzymol. 182, 50-68 (1990)). Colorimetric protein quantitation assays, including the Bradford and Lowry methods, are frequently used due to their sensitivity and quick procedures (Olson, B.J.S.C. & Markwell, J. Assays for determination of protein concentration. in Curr. Protoc. Protein Sci. (eds. Coligan, J.E., Dunn, B.M., Speicher, D.W., Wingfield, P.T. & Ploegh, H.L.) 3.4.1-3.4.29 (John Wiley & Sons, Inc., New York, 2007); Dunn, B. Quantitative amino acid analysis. in Curr. Protoc. Protein Sci. (eds. Coligan, J.E., Dunn, B.M., Speicher, D.W., Wingfield, P.T. & Ploegh, H.L.) 3.2.1-3.2.3 (John Wiley & Sons, Inc., New York 2000)). However, accuracy of colorimetric methods depends on the protein and these methods require standards for obtaining actual concentration values (Olson, B.J.S.C. & Markwell, J. Assays for determination of protein concentration. in Curr. Protoc. Protein Sci. (eds. Coligan, J.E., Dunn, B.M., Speicher, D.W., Wingfield, P.T. & Ploegh, H.L.) 3.4.1-3.4.29 (John Wiley & Sons, Inc., New York, 2007); Stoscheck, C.M. Quantitation of proteins. Methods Enzymol. 182, 50-68 (1990)). The PHA method is a colorimetric technique for quantifying proteins containing intrinsic heme and is the most utilized method for this purpose (Sinclair, P.R., Gorman, N. & Jacobs, J. M. Measurement of heme concentration. in Curr. Protoc. Toxicol. (eds. Maines, M. et al.) 8.3.1-8.3.7 (John Wiley & Sons, Inc., New York 1999)).

This example demonstrates that the purification of proteins using the heme-tag-HIS method offers the additional advantage in that the proteins can be easily quantified using the PHA. Unlike other colorimetric techniques, the PHA method does not require standardization and depends only on the presence of heme, thus lending the PHA methods use to any protein containing a heme tag. In addition, $\epsilon^P_{280}$ was estimated for Az and MBP using the concentration determined from the PHA without removing the heme tag from Az-Hm14 and MBP-Hm16. The results of example show that $\epsilon^P_{280}$ measured for Az and MBP are comparable to those higher values used in the literature for Az and MBP, and thus represent a method useful for estimating $\epsilon^P_{280}$ for Az and MBP.

The HIS method for purification disclosed herein uses ligand-metal coordination to bind the protein to the chromatography matrix. Thus, in preferred embodiments, additives that interfere with metal-imidazole binding should be avoided. This also applies to the His-tag-IMAC method.

The appearance of a green band that did not bind the HIS resin suggests that some degradation of the heme tag by *E. coli* heme oxygenases occurs, which can lower the yield of purified heme-tagged proteins. Thus to avoid this problem, in preferred embodiments, the amount of oxygenation of the culture can be limited, and/or the growth can be supplemented with metalloporphyrins known to inhibit heme oxygenase activity (Suits, M.D.L. et al. Identification of an *Escherichia coli* O157: H7 heme oxygenase with tandem functional repeats. Proc. Natl. Acad. Sci. U.S.A. 102, 16955-16960 (2005); Appleton, S.D. et al. Selective inhibition of heme oxygenase, without inhibition of nitric oxide synthase or soluble guanylyl cyclase, by metalloporphyrins at low concentrations. Drug Metab. Dispos. 27, 1214-1219 (1999)). Furthermore, in preferred embodiments of the PHA method for protein quantitation disclosed herein, use of a sensitive spectrophotometer is preferred (Sinclair, P.R., Gorman, N. & Jacobs, J. M. Measurement of heme concentration. in Curr. Protoc. Toxicol. (eds. Maines, M. et al.) 8.3.1-8.3.7 (John Wiley & Sons, Inc., New York 1999)).

In summary, this example demonstrates an affinity purification and quantitation method for proteins that can be expressed in *E. coli*. In addition, this example demonstrates that a metal-containing affinity tag that uses coordination to a ligand-immobilized chromatography resin can be used for protein purification. Unlike the case for the His-tag-IMAC and the MBP-amylose methods commonly used in the art, non-specific binding of untagged proteins does not present a significant problem for the heme tag-HIS method for the protein purification used in this example. Additionally, the heme tag's strong visible absorbance allows for continuous tracking, detecting, and quantitation of any recombinant protein expressed in E. coli.

6.1.6. Methods 6.1.6.1. Heme-Tagged Protein Constructs and Cloning.

The procedures for plasmid construction and cloning are described in Section 6.1.7 (Supplementary Methods) below.

6.1.6.2. Protein Overexpression and Partial Clarification

The expression vectors carrying the heme-tagged Az variants used in this example were individually transformed along with pEC86 (carrying ccmABCDEFGH) (Arslan, E., Schulz, H., Zufferey, R., Kunzler, P. & Thöny-Meyer, L. Overproduction of the Bradyrhizobium japonicum c-type cytochrome subunits of the cbb(3) oxidase in Escherichia coli. Biochem. Biophys. Res. Commun 251, 744-747 (1998)) into BL21* (DE3) E. coli (Invitrogen) and grown with shaking (160-170 rpm) at 25-28° C. in Luria-Bertini (LB) medium containing 50 mg/L of ampicillin (Amp) and chloramphenicol (CM). The pEC86 plasmid is known in the art (Arslan, E., Schulz, H., Zufferey, R., Kunzler, P. & Thöny-Meyer, L. Overproduction of the Bradyrhizobium japonicum c-type cytochrome subunits of the cbb(3) oxidase in Escherichia coli. Biochem. Biophys. Res. Commun. 251, 744-747 (1998)). The cells were grown for 16 hours and harvested by centrifugation at 10,000 rpm 4-5 hours after induction with 0.4-mM IPTG. The cell pellets were stored at −20° C. until further use. The cellular extracts containing each heme-tagged Az variant used in this example were prepared using the same procedures. Briefly, the cellular proteins were extracted by resuspending the cell paste in 50 mM tris, 4 mg/mL lysozyme, and 1.5 units/mL DNAase I (Sigma), pH 8.0. The lysis suspension was incubated for one hour at 30° C. following centrifugation at 10,000 rpm for 20 minutes to separate the extract from the cellular components. The supernatant pH was increased to 8.8-9.0 using 1 M NaOH and loaded on a DEAE Sepharose (GE Healthcare, Piscataway, N.J.) pre-equilibrated with 20 mM tris, pH 8.8. The column was washed with 10 CV of the same buffer and eluted with 20 mM tris, pH 8.8, 200 mM NaCl buffer. Alternatively, the protein was eluted from the column using a gradient of 10-50% 20 mM tris, 200 mM NaCl, pH 8.8. The eluted extract was concentrated in an Amicon® (Millipore, Billerica, Mass.) to 4 mL and exchanged in 50 mM sodium phosphate buffer, pH 7.0 using a PD-10 desalting column (GE Healthcare) before loading on the HIS resin. The same transformation procedure and E. coli strain used for the expression of heme tagged Az constructs was used for expressing MBP-Hm16 transcribed from the pMALHm16 vector. The cells were grown for 7-8 hours and harvested 17 hours after induction with 0.4-mM IPTG at 37° C. by centrifugation at 10000 rpm. The cell pellets were stored at −20° C. until further use. The periplasmic extract was isolated using a cold osmotic shock protocol followed as described by Riggs (Riggs, P. Expression and purification of maltose-binding protein fusions. in Curr. Protoc. Mol. Biol. (eds. Ausubel, F.M. et al.) 16.6.1-16.6.14 (John Wiley & Sons, Inc., New York, 1994)). The periplasm was concentrated and exchanged into the HIS resin binding buffer as described for the heme-tagged Az variants.

6.1.6.3. Histidine Immobilized Sepharose Preparation.

A prepacked 5-mL HiTrap™ NHS-activated HP column (GE Healthcare) was covalently coupled with L-histidine by adding 1 CV of 10 mg/mL L-histidine (Sigma), 20 mM $NaHCO_3$, 0.5 M NaCl, pH 8.3. The coupling reaction and subsequent cleanup was performed as recommended by the manufacturer. Alternatively, 25 mL of NHS-activated Sepharose 4 Fast Flow resin was coupled in the same manner and loaded into a 2.5×10-cm low pressure glass column (Bio-Rad, Hercules, Calif.).

6.1.6.4. Absorption Spectroscopy and Pyridine Hemochrome Assay.

Ultraviolet-visible (UV-vis) absorption spectra were taken on a Shimadzu UV-2401PC spectrophotometer at room temperature. The pyridine hemochrome samples were prepared as follows: 80 mL stock protein solution (dissolved in 50 mM $NaP_i$, pH 7.0), 910 mL pyridine solution (100 mM NaOH, 20% v/v pyridine, 50 mM $NaP_i$), 10 mL saturated dithionite solution (>1.0 M sodium dithionite, 50 mM $NaP_i$). Each sample was prepared in triplicate and the spectra taken immediately after addition of the dithionite solution. The concentration of protein was calculated using the extinction coefficient for c-type heme in pyridine buffer of 30.27 $mM^{-1}$ $cm^{-1}$ at 550 mM as reported by Berry & Trumpower (Berry, E.A. & Trumpower, B. L. Simultaneous determination of hemes-a, hemes-b, and hemes-c from pyridine hemochrome spectra. Anal. Biochem. 161, 1-15 (1987)). The average concentration of the reduced PHA samples was used to calculate extinction coefficients at different wavelengths for the spectra of the oxidized samples. Oxidized samples without exogenous ligand to heme were prepared as described above for the PHA samples, except that 920 mL of 50 mM $NaP_i$, pH 7.0 was used instead of the pyridine and dithionite solutions. Cyanide-ligated derivatives of the samples were prepared by adding 60-70 mM NaCN to the oxidized samples, with the pH adjusted to 7.1 using 1 M HCl. The stock protein solutions were oxidized with excess $K_3[Fe(CN)_6]$ and exchanged in 50 mM $NaP_i$, pH 7.0 using a PD-10 desalting column (GE-Healthcare) before any samples were prepared.

6.1.7. Supplementary Methods 6.1.7.1. General Techniques

Recombinant DNA manipulations were carried out according to standard protocols. (Sambrook J, Fritsch EF, Maniatis T (1989) Molecular Cloning. A Laboratory Manual, 2nd ed. Cold Spring Harbor Laboratory Press, Cold Spring Harbor, N.Y.). All plasmid constructs were confirmed by DNA sequencing using the T7 or malE promoter primer (University of Rochester Functional Genomics Center, Rochester, N.Y.). Cloning was performed using E. coli strain XL1-Blue (Stratagene, Agilent Technologies, Santa Clara, Calif.). SDS-PAGE analysis was performed as described by Laemmli (Laemmli UK (1970) Cleavage of structural proteins during the assembly of the head of bacteriophage T4. Nature 227: 680-685.) In-gel proteins were treated with 1% w/v Coomassie brilliant blue, 40% v/v methanol, and 10% v/v glacial acetic acid for 30 minutes. Excess stain was removed by treating the stained gels with 40% v/v methanol, and 10% v/v acetic acid for approximately four hours with agitation. Gels that were stained for peroxidase activity (heme stain) were fixed with 12.5% trichloroacetic acid (Sigma-Aldrich, St. Louis, Mo.) for 30 minutes and then washed with water for 30 minutes. The heme staining procedure was followed as described, but with minor modifications. (Francis RT, Becker RR (1984) Specific indication of hemoproteins in polyacrylamide gels using a double-staining process. Anal. Biochem. 136: 509-514). Briefly, the fixed gels were immersed in a solution of 20 mL o-dianisidine solution (0.2 g o-dianisidine (Sigma), 20 mL glacial acetic acid), 20 mL 0.5 sodium citrate, pH 4.3, 0.4 mL 30% hydrogen peroxide, and 160 mL water for 30-60 min.

6.1.7.2. pETAzHm14 Plasmid Construction

The pET-9a plasmid (Novagen, Merck, Whitehouse Station, N.J.) carrying the *Pseudomonas aeruginosa* azurin structural gene (azu) with preceding signal sequence for translocation to the periplasm was used (Chang, T. K. et al. Gene synthesis, expression, and mutagenesis of the blue copper proteins azurin and plastocyanin. Proceedings of the National Academy of Sciences of the United States of America 88, 1325-1329 (1991). The complete signal sequence and azu, minus the last four codons, was excised from pET-9a by digestion with NdeI and KpnI and cloned into pET-17b, resulting in the pET-17b(azu) vector. The 78-bp Hm14 sequence (5'-ATGAAAGGTACCCTGACTCT-GAAAGGCGCCACCAGCTGCG CGGCGTGCCATGCG-GATAGCGAACATTAAACTAGT-3') (SEQ ID NO:13) was synthesized by Integrated DNA Technologies, Inc. (Coralville, Iowa) and amplified by PCR using the primers Hm14 Fwd (5'-ATGAAAGGTACCCTGACTCTGAAAGGCGCC-3') (SEQ ID NO:14) and Hm14 Bwd (5'-ATCAG TTTAAT-GTTCGCTATGCGCATGCG-3') (SEQ ID NO:15). The fragment, which includes the last four codons of azu followed by the heme tag sequence, was inserted into pET-17b(azu) using the KpnI and SpeI restriction sites, resulting in the complete Az-Hm14 fusion in pET-17b, pETAzHm14. The initial Hm14 tag design included a His residue as the last amino acid of the tag, which was intended to provide the sixth axial ligand to the heme iron. However, this variant had five-coordinate heme according to UV-vis analysis, and instead a heme tag containing a polyhistidine sequence was used to achieve six-coordinate heme (see below). For our final Hm14 construct, the His in the original tag design was mutated to an arginine residue in the pETASAHm14 plasmid to ensure an unobstructed coordination site for ligand binding using the mutagenic primers H14*RP1 (5'-GCCATGCGGATAGC-GAACGTTAAACTAGTAACG GCCGC-3') (SEQ ID NO:16) and H14*RP2 (5'CGCGCCGTTACTAGTTTA ACGTTCGCTATCCGCATGGC-3') (SEQ ID NO:17) using QuikChange (Stratagene) methods.

6.1.7.3. pETAzHm-MP301 Plasmid Construction

The pETAzHm-MP301 vector coding for the Az-MP301 variant (incorporating the heme tag sequence reported by Thöny-Meyer and coworkers) (Braun, M., Rubio, I.G. & Thöny-Meyer, L. A heme tag for in vivo synthesis of artificial cytochromes. Appl. Microbiol. Biotechnol. 67, 234-239 (2005)) used in this example was constructed as described for pETAzHm14 vector except that the MP301 sequence was used instead of Hm14. The 78-bp MP301 sequence (5'-AT-GAAAGGTACCCTGACTGTGAAAAACAGC-CGTTATCCGGCGGC GTGCCTGGCGTGCCATGCGAT-TGGCTAAACTAGT-3') (SEQ ID NO:18) was synthesized by Integrated DNA Technologies, Inc. and amplified by PCR using the primers MP301 Fwd (5'-ATGAAAGGTACCCT-GACTCTGAAAAACAGCCG-3') (SEQ ID NO:19) and MP301 Bwd (5'-ACTAGTTTAGCCAATCGCATG-GCACGCCAGG-3') (SEQ ID NO:20).

6.1.7.4. MBP-Hm16 Cloning and Purification Using Amylose Method.

The pMALHm16 vector coding for MBP-Hm16 is derived from pMALp4x (purchased from New England Biolabs) following manufacturer's instructions. The sequence (5'-GAAGCGACCTGCGCGCAGTGCCACGC-GACCGCGGATGCGTGCGCG CAGTGCCACGCGACCGCGGATGCGT-GCGCGCAGTGCCACACCGCGGAATAAAAGCT TATATAT-3') (SEQ ID NO:21) was synthesized by Integrated DNA Technologies, Inc., amplified by PCR using the primers Hm31 Fwd (5'-GAAGCGACCTGCGCGCAGTGC CACGCGACC-3') (SEQ ID NO:22) and Hm31 Bwd (5'-ATATATAAGCTTTTATTCCGCGGTGTGGC ACT-GCGCGC-3') (SEQ ID NO:23) and inserted into pMALp4x (New England BioLabs) using the XmnI and HindIII restriction sites as recommended by the manufacturer. Next, an ochre stop codon was introduced at position 17 of the inserted sequence in using the mutagenic primers MBPstp1 (5'-CACGCGACCGCGGATTAAT GCGCGGA GTGCCACG-3') (SEQ ID NO:24) and MBPstp2 (5'-CGTGGCACTGCGC GCATTAATCC GCGGTCGCGTG-3') (SEQ ID NO:25) using QuikChange (Stratagene) methods, resulting in the pMALHm16 plasmid. The parent pMALp4x vector is comprised of the MBP structural gene (malE) and native signal sequence with a carboxyl-terminal factor Xa protease (fXa) site sequence. The final construct resulted in malE gene fused with a 16 amino acid peptide tag with one heme attachment motif.

In addition to being purified using the HIS method, MBP-Hm16 was purified using an amylose resin as described by the pMAL™ Protein Fusion and Purification System instruction manual (New England BioLabs). Briefly, the concentrated periplasmic extract was loaded on 10 mL of amylose resin (New England BioLabs) in a 1.5×8-cm column equilibrated with 20 mM Tris-HCl, 200 mM NaCl, 1 mM EDTA pH 7.4 (amylose-binding buffer). The column was washed with 12 CV of amylose-binding buffer as recommended before eluting with the same buffer containing 10 mM D(+)-maltose. The flow rate of the column used for each step of the purification was ~1 mL/min.

6.1.7.5. Az-Hm20 Cloning and Purification Using IMAC

The pETAzHm20 vector coding for the Az-Hm20 variant used in this example was constructed as described for pETAzHm14 vector except that the Hm20 sequence was used instead of Hm14. The 93-bp Hm20 sequence (5'-ATGAAAG-GTACCCTGACTCTGAAAGGCGCCAC-CAGCTGCGCGGCGTGCCA TGCGGATAGCGAACAT-CATCATCATCATCATTAAACTAGT-3') (SEQ ID NO:26) was synthesized by Integrated DNA Technologies, Inc. and amplified by PCR using the primers Hm20 Fwd (5'-AT-GAAAGGTACCCTGACTCTGAAAGGCGCC-3') (SEQ ID NO:27) and Hm20 Bwd (5'-ACTAGTTTAATGATGATGAT-GATGATGATGTTCGCTATCCGC-3') (SEQ ID NO:28). The overexpression and preparation of the cellular extract containing Az-Hm20 was followed exactly as for Az-Hm14 (see main text).

To purify Az-Hm20 by IMAC for comparison to the heme-tag/HIS method, 3-5 mL of partially clarified extract was added to 8 mL of Ni(II)-loaded IMAC resin (GE-Healthcare) in a 1.5×8-cm column equilibrated with 25 mM $NaP_i$, 1 M NaCl, 60 mM imidazole pH 8.0 (IMAC-binding buffer). The column was washed with 9 CV of IMAC-binding buffer before eluting with 2 CV of 25 mM $NaP_i$, 0.5 M NaCl, 500 mM imidazole pH 8.0. The flow rate of the column used for each step of the purification was ~1 mL/min.

6.1.7.6. Azurin, Horse Heart Myoglobin and Cytochrome c Preparation.

Horse heart myoglobin and horse heart cytochrome c were purchased from Sigma and used without additional purification. Pure Cu(II)Az was obtained by using methods known in the art. The purification protocol used to obtain the pure Cu(II)Az has been previously described in Vandekamp M, Hali FC, Rosato N, Agro AF, Canters GW (1990) Purification and characterization of a nonreconstitutable azurin, obtained by heterologous expression of the *Pseudomonas aeruginosa* azu gene in *Escherichia coli*. Biochimica Et Biophysica Acta 1019: 283-292, and was followed with minor alterations.

6.1.7.7. Microperoxidase-8 Preparation and Purification

Microperoxidase-8 (MP8) was prepared by pepsin (Sigma) and trypsin (Sigma) digestion of horse heart cytochrome c (Sigma). The reaction conditions were followed as recommended by the literature (Low DW, Winkler JR, Gray HB (1996) Photoinduced oxidation of microperoxidase-8: Generation of ferryl and cation-radical porphyrins. J. Am. Chem. Soc. 118: 117-120). MP8 was purified using the 5-mL HIS column, and verified by SDS-PAGE analysis using pre-cast 15% tris-tricine polyacrylamide gels (BioRad).

6.2. Example 2

Further Use of a Heme Fusion Tag for Protein Purification and Quantitation

Enzymatic cleavage of affinity tags is frequently used for obtaining pure non-tagged recombinant protein. In this example, a endoprotease cleavage site recognized by factor Xa (fXa) was included in an Az-Hm14 construct (Az-fXa-Hm14) for cleavage of the heme tag after purification using the HIS method. Az-fXa-Hm14 contains the Ile-Asp-Gly-Arg (IDGR) fXa cleavage motif as the linker between Az and the CXXCH motif carrying the covalently bound heme chromophore as shown below:

Azurin-IDGR↓CAACHADSER (SEQ ID NO:29)

fXa will cleave the tag after the arginine residue of the IDGR cleavage motif. For clarity, the location of cleavage is shown above using a downward pointing arrow. Construction of the pETAz-fXa-Hm14 plasmid carrying the Az-fXa-Hm14 variant was followed as described for pETAzHm14. Az-fXa-Hm14 was expressed and purified as described for Az-Hm14.

To remove the tag, Az-fXa-Hm14 was incubated with fXa (New England Biolabs) following the procedure recommended by the manufacturer. The fXa-digested Az-fXa-Hm14 was run against pure native Az (MW=14 kDa) and pure, uncleaved Az-fXa-Hm14 (MW=15 kDa) on a 15% SDS-PAGE gel visualized by Coomassie blue. Two bands were detected for the cleaved Az-fXa-Hm14, one intense band with the same molecular weight as native Az, and another less intense band with the same molecular weight as pure Az-fXa-Hm14. The appearance of a band at the same weight of native-untagged Az suggests that the heme tag was cleaved after fXa digestion. The fXa-digested Az-fXa-Hm14 was loaded onto the HIS resin to remove the cleaved heme-tagged peptide and residual non-cleaved Az-fXa-Hm14. The column was washed with binding buffer to bind the heme-containing products of the fXa digestion (heme tag peptide, and non-cleaved Az-fXa-Hm14). A red band formed at the top of the column after addition of binding buffer as expected, indicating that the heme-containing components were immobilized on the column. The de-tagged Az was collected after the addition of approximately 0.8 CV of binding buffer. The estimated cleavage yield based on the gel is 75%.

6.3. Example 3

N-Terminus Tagging a Protein of Interest

This example demonstrates the tagging of a test protein of interest, azurin, at its N-terminus and demonstrating its purification on a HIS column.

A construct was employed that had the heme tag sequence immediately following the N-terminal signal sequence:

Signal sequence-linker-CXXCH-linker-target protein

FIG. 10 shows photographs of N-terminally tagged azurin bound to the HIS column after several column volumes (CV) of added binding buffer (BB). The affinity for the resin appeared to be higher than the C-terminally tagged variants because there was no detected migration on the column with added binding buffer for this N-terminally tagged azurin.

Affinity for the column was high, as the red band of heme-tagged protein stuck to the column through many column volumes of 50 mM sodium phosphate, pH 7.0 binding buffer (BB; FIG. 10). This differs from what was observed previously with C-terminal constructs, which show a small amount of migration on the column with washing. The purity of the product was excellent (typically was 5-6 mg/L bacterial culture) as was the case with the C-terminal constructs.

6.4. Example 4

Protein Fold of Heme-Tagged Protein

NMR spectra ($^1$H-$^{15}$N HSQC) of heme-tagged azurin were collected that show that the protein is well-folded after heme-tagging. FIG. 11 shows 500-MHz NMR spectra ($^1$H-$^{15}$N HSQC) of heme-tagged azurin with added imidazole. The peak dispersion shows that the protein is well-folded after heme-tagging. The spectra shown are from heme-tagged azurin with added imidazole. Since in this example, minimal medium was used to express the protein, this result shows that the heme attachment proceeds in minimal medium as well as rich medium.

6.5. Example 5

Molecular Mass of Heme-Tagged Protein

Mass spectra of a number of heme-tagged proteins were collected. The molecular mass was as expected for the constructs. The MALDI-TOF mass spectrum of the N-terminally tagged azurin variant is representative of these data (FIG. 12). Measured mass: 16377 Da. Expected mass: 16300 Da. Difference in measured and expected may result from uncertainty in signal peptide cleavage, and in experimental error from the mass spectral analysis. However, the overall mass was consistent with fusion of the heme-tag peptide and binding of the heme to this peptide.

6.6. Example 6

Heme Tag Cleavage

This example demonstrates cleavage of the heme tag from azurin using the endopeptidase factor Xa. The untagged protein was easily separated from the tagged protein by using a HIS column, to which the untagged protein does not bind. FIG. 13 shows SDS-PAGE results demonstrating cleavage of heme tag from azurin using the factor Xa endopeptidase. Lane 1: non-cleaved heme-tagged azurin; Lane 2: heme-tagged azurin digested with factor Xa showing cleaved protein and cleaved heme-tagged peptide; Lane 3: blank; lane 4: cleaved (non-tagged) azurin obtained by washing digested protein through the HIS column (HIS column binds cleaved heme tag peptide and does not bind the cleaved non-tagged protein product); Lane 5: Blank; Lane 6 and 7: cleaved heme tag peptide obtained from the HIS column after washing the resin with imidizole. This SDS-PAGE gel demonstrates that the heme-tags containing the factor Xa recognition site appended to the proteins can be cleaved by digesting the tagged proteins with the enzyme.

6.7. Example 7

Heme Tag Fusions

This example sets forth exemplary heme tags that bind heme (Table 3). The diversity of tag designs demonstrates that the heme tag fusion system has great flexibility and that heme tags can be readily designed that are optimized for charge, solubility, etc. All of the 5-coordinate heme tags in Table 3 were observed to be capable of binding exogenous ligands and can be used for binding to the HIS column. Those tags listed as 6-coordinate tags (including the di-heme tag which has 1 5-coordinate and 1 6-coordinate heme) were purified using a Ni(II) IMAC affinity resin. The 5-coordinate heme-tagged proteins, with the exception of the construct with 2 hemes, were purified using the HIS resin. The CXXCH motif is underlined for each tag sequence.

TABLE 3

Heme tags that bind heme.

| Heme-Iron Coordination | Heme Tag Peptide Sequence |
|---|---|
| 5 | GATSCAACHADSER (SEQ ID NO: 9) |
| 5 | GATSECAACHADSER (SEQ ID NO: 30) |
| 5 | GATSERCAACHADSER (SEQ ID NO: 31) |
| 5 | GATSERDCAACHADSER (SEQ ID NO: 32) |
| 6 | GATSCAACHADSEHHHHHHH (SEQ ID NO: 33) |
| 5 | RESDACAACHSRGSTG (SEQ ID NO: 34) |
| 5 | IEGREATCAQCHATAD (SEQ ID NO: 11) |
| 5,6 | VEAFEKKCAECHSKVAAFESKCAECHHHHHH (SEQ ID NO: 35) |
| 5 | VEAFEKKVAAFESKCAACHAK (SEQ ID NO: 36) |
| 5 | GYASCWACHEEEE (SEQ ID NO: 37) |
| 5 | HSSYWYAFNNKTGCAACHEEEE (SEQ ID NO: 38) |

6.8. Example 8

Heme-Tagging in the *E. coli* Cytoplasm

This example demonstrates an embodiment of the method for heme-tagging proteins, in which proteins of interest are heme-tagged in the *E. coli* cytoplasm. Some of the embodiments of the heme-tagging method disclosed above can require export of the protein of interest to periplasm for heme-tagging. This step may be a limitation with some proteins, in particular large proteins. With cytoplasmic tagging, export is not required. Expression of full-length cytochromes c and maturation (heme attachment) in the cytoplasm was reported previously (Pollock et al., Biochemistry 1998, 37, 6124-6131).

Cytochrome c structural protein without a signal sequence and the enzyme *Saccharomyces cerevisiae* cytochrome c heme lyase can be coexpressed. The lyase attaches the heme to the polypeptide and has been shown to function in the cytoplasm of *E. coli*. This system, however, does not have broad use because the heme lyase has only been shown to attach heme to mitochondrial cytochromes c, and thus is not expected to attach heme to some heme tag designs. However, it was reported by Veloso et al., (J. Biol. Chem. 1984, 259, 6067-6073) that mixing a synthetic peptide corresponding to the 25 N-terminal amino acids of mitochondrial cytochrome c with mitochondrial extract yields peptide with heme covalently attached, indicating that the N-terminal region contains the necessary recognition elements for recognition by heme lyase (and any other unidentified factors facilitating heme attachment.

In this example, the N-terminal 29 amino acids of mitochondrial (horse) cytochrome c were fused to the N-terminus of the target protein (PSD95-PDZ3 domain protein, 10 kDa, 93 amino acids):

(SEQ ID NO: 7)
GDVEKGKKIFVQKCAQCHTVEKGGKHKTG-PDZ3 Domain and the fusion was co-expressed in *E. coli* along with the heme lyase gene. The heme attached based on recognition of the 29 amino acid N-terminal fusion. This heme-tagged protein was then subjected to chromatography on a HIS column as with proteins heme-tagged in the periplasm as described hereinabove.

To test whether heme attachment occurs to the PDZ3 domain protein fused with the 29 residue N-terminus of horse cytochrome c, the fusion protein was co-expressed along with the heme lyase gene. FIG. 14 is a photograph of bacterial pellets containing expressed PDZ3 domain protein variants. (Left) Pellet containing wild-type PDZ3 domain (non-heme tagged). The color of the pellet was what was expected for expression of a non-heme containing protein. (Middle) Pellet containing PDZ3 domain tagged with the first 29 residues of horse cytochrome c. The brownish-red color was what was expected for a five-coordinate heme containing protein. (Right) Pellet containing wild-type horse cyt c. The bright red color was what was expected for the complete expression of six-coordinate heme containing cytochrome c.

To show that the pellet (middle, FIG. 14) contained an overexpressed heme protein, the pellet was disrupted and the cell lysate obtained containing the PDZ3 domain with the 29 residue heme tag. The lysate had a dark orange color as was expected for heme-containing material (FIG. 15B), and the UV-Vis spectrum for the lysate indicated the presence of an overexpressed heme protein (FIG. 15A).

These results demonstrate that heme lyase is capable of recognizing and covalently modifying the 29 residue tag with heme in the cytoplasm, allowing for cytoplasmic expression of heme-tagged proteins.

The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

All references cited herein are incorporated herein by reference in their entirety and for all purposes to the same extent as if each individual publication, patent or patent application was specifically and individually indicated to be incorporated by reference in its entirety for all purposes.

The citation of any publication is for its disclosure prior to the filing date and should not be construed as an admission that the present invention is not entitled to antedate such publication by virtue of prior invention.

What is claimed is:

1. A method for purifying a protein or peptide of interest providing a heme tag with an open coordination site;
tagging the protein or peptide of interest with the heme tag;
providing a resin framework, wherein:
a base that binds to heme is immobilized to the resin, and
the open coordination site of the heme tag is capable of reversibly binding to the base immobilized to the resin; and
reversibly binding the tagged protein or peptide of interest to the resin.

2. The method of claim 1 comprising, after the step of reversibly binding the tagged protein or peptide of interest to the resin, the step of:
eluting the protein or peptide of interest from the resin.

3. The method of claim 2 comprising, after the step of eluting the protein or peptide of interest from the resin, the step of:
quantitating the eluted protein or peptide.

4. The method of claim 1 comprising the step of estimating or determining $\epsilon^P_{280}$.

5. The method of claim 1 wherein the protein or peptide of interest is expressed in a bacterial or yeast expression system.

6. A method for identifying secretion of a protein or peptide of interest to the periplasm comprising the steps of:
providing a heme tag sequence fused to a protein or peptide of interest, wherein the heme tag sequence encodes a peptide that comprises a CXXCH motif;
attaching heme to the heme tag sequence with a cytochrome c maturation apparatus from a bacterium, thereby tagging the protein or peptide of interest with a heme tag;
expressing the protein or peptide of interest in an expression system; and
screening for color change in the periplasm, wherein the color change is indicative of secretion of the protein or peptide of interest to the periplasm.

7. The method of claim 6 wherein the protein or peptide of interest is expressed in a bacterial or yeast expression system.

8. The method of claim 6 wherein the heme-tagged proteins or peptides are exported to periplasm via the twin-arginine translocation (Tat) system.

9. A method for cytoplasmic tagging of a protein or peptide of interest comprising the steps of:
providing a heme tag sequence fused to a protein or peptide of interest, wherein the heme tag sequence encodes a peptide that comprises a CXXCH motif and wherein the heme tag sequence is solvent-exposed;
providing a fusion construct encoding a fusion protein wherein the N-terminal amino acids of mitochondrial cytochrome c are fused to the N-terminus of the protein or peptide of interest; and
co-expressing the fusion construct and heme lyase gene in an expression system, thereby producing a heme-tagged fusion protein or peptide in the cytoplasm.

10. The method of claim 9 wherein the mitochondrial cytochrome c is capable of being expressed in the expression system using heme lyase for maturation.

11. The method of claim 9 wherein the expression system is a bacterial or yeast expression system.

12. The method of claim 11 comprising the step of screening for color change in the bacteria or yeast, wherein the color change is indicative of cytoplasmic tagging of the protein or peptide of interest.

13. The method of claim 9 further comprising the steps of:
providing a resin framework, wherein:
a base that binds to heme is immobilized to the resin, and
the heme tag comprises an open coordination site, wherein the open coordination site is capable of reversibly binding to the base immobilized to the resin; and
reversibly binding the tagged protein of interest to the resin.

14. The method of claim 13 comprising, after the step of reversibly binding the tagged protein of interest to the resin, the step of:
eluting the protein of interest from the resin.

15. The method of claim 14 comprising, after the step of eluting the protein of interest from the resin, the step of:
quantitating the eluted protein.

16. A method for quantitating a protein or peptide of interest comprising the steps of:
providing a heme tag with an open coordination site;
tagging the protein or peptide of interest with the heme tag;
providing a resin framework, wherein:
a base that binds to heme is immobilized to the resin, and
the open coordination site of the heme tag is capable of reversibly binding
to the base immobilized to the resin;
reversibly binding the tagged protein or peptide of interest to the resin;
eluting the protein or peptide of interest from the resin; and
performing heme quantitation on the eluted protein or peptide, wherein the step of heme quantitation does not remove the heme tag.

17. A method for determining the extinction coefficient of a protein or peptide of interest at 280 nm ($\epsilon_{280}$) comprising:
heme-tagging the protein or peptide of interest with a heme tag, wherein the heme tag sequence is solvent-exposed;
performing a pyridine hemochrome assay on the heme-tagged protein or peptide;
subtracting the absorbance of the heme-tagged protein or peptide at 280 nm from absorbance of the heme tag at 280 nm to determine a remaining absorbance at 280 nm;
using the remaining absorbance at 280 nm to determine the protein's or peptide's $\epsilon_{280}$ through the relationship to a concentration determined from an extinction coefficient determined at 550 nm by the pyridine hemochrome assay.

18. A peptide fusion system comprising a heme tag, said heme tag comprising:
a heme tag sequence fused to a protein or peptide of interest, wherein the heme tag sequence encodes a peptide that comprises a CXXCH motif, and wherein the heme tag is solvent exposed; and a heme attached to the heme tag sequence.

19. A method for cytoplasmic tagging of a protein or peptide of interest comprising the steps of:
the heme tag sequence encodes a peptide that comprises a CXXCH;
providing a fusion construct encoding a fusion protein wherein the N-terminal amino acids of mitochondrial cytochrome c are fused to the N-terminus of the protein or peptide of interest;
co-expressing the fusion construct and heme lyase gene in an expression system, thereby producing a heme-tagged fusion protein or a heme-tagged fusion peptide in the cytoplasm;
providing a resin framework, wherein:
a base that binds to heme is immobilized to the resin, and
the heme tag comprises an open coordination site, wherein the open coordination site is capable of reversibly binding to the base immobilized to the resin; and
reversibly binding the tagged protein or tagged peptide of interest to the resin.

20. The method of claim 19 comprising, after the step of reversibly binding the tagged protein or tagged peptide of interest to the resin, the step of:
eluting the protein or peptide of interest from the resin.

21. The method of claim 20 comprising, after the step of eluting the protein or peptide of interest from the resin, the step of:
quantitating the eluted protein or peptide.

22. The method of claim 1, wherein the base that binds to heme is an imidazole, amine, pyridine, cyanide, or isocyanide or a derivative thereof.

23. The method of claim 13, wherein the base that binds to heme is an imidazole, amine, pyridine, cyanide, or isocyanide or a derivative thereof.

24. The method of claim 16, wherein the base that binds to heme is an imidazole, amine, pyridine, cyanide, or isocyanide or a derivative thereof.

25. The method of claim 19, wherein the base that binds to heme is an imidazole, amine, pyridine, cyanide, or isocyanide or a derivative thereof.

* * * * *

UNITED STATES PATENT AND TRADEMARK OFFICE
CERTIFICATE OF CORRECTION

PATENT NO. : 8,815,533 B2  
APPLICATION NO. : 13/576038  
DATED : August 26, 2014  
INVENTOR(S) : Kara L. Bren et al.

Page 1 of 1

It is certified that error appears in the above-identified patent and that said Letters Patent is hereby corrected as shown below:

In the Claims

Claim 1, Col. 45, Line 37, after word "interest" insert --comprising the steps of:--

Claim 8, Col. 46, Line 43, delete "wherein the" and replace with --wherein--

Claim 13, Col. 47, Line 7, after word "protein" insert --or peptide--

Claim 14, Col. 47, Line 10, after word "protein" insert --or peptide--

Claim 14, Col. 47, Line 12, after word "protein" insert --or peptide--

Claim 15, Col. 47, Line 14, after word "protein" insert --or peptide--

Claim 15, Col. 47, Line 15, after word "protein" insert --or peptide--

Claim 19, Col. 48, Line 7, after words "steps of:" insert --providing a heme tag sequence fused to a protein or peptide of interest, wherein--

Signed and Sealed this  
Twenty-fifth Day of November, 2014

Michelle K. Lee  
*Deputy Director of the United States Patent and Trademark Office*